US012280176B2

(12) United States Patent
Voytik-Harbin

(10) Patent No.: US 12,280,176 B2
(45) Date of Patent: Apr. 22, 2025

(54) METHODS AND COMPOSITIONS FOR MATRIX PREPARATION

(71) Applicant: GENIPHYS, INC., Zionsville, IN (US)

(72) Inventor: Sherry L. Voytik-Harbin, Zionsville, IN (US)

(73) Assignee: GENIPHYS, INC., Zionsville, IN (US)

( * ) Notice: Subject to any disclaimer, the term of this patent is extended or adjusted under 35 U.S.C. 154(b) by 0 days.

(21) Appl. No.: 16/482,465

(22) PCT Filed: Jan. 31, 2018

(86) PCT No.: PCT/US2018/016069
§ 371 (c)(1),
(2) Date: Jul. 31, 2019

(87) PCT Pub. No.: WO2018/144496
PCT Pub. Date: Aug. 9, 2018

(65) Prior Publication Data
US 2020/0246507 A1 Aug. 6, 2020

Related U.S. Application Data

(60) Provisional application No. 62/452,564, filed on Jan. 31, 2017.

(51) Int. Cl.
A61L 27/36 (2006.01)
A61L 2/00 (2006.01)
C07K 14/78 (2006.01)

(52) U.S. Cl.
CPC ......... *A61L 27/3633* (2013.01); *A61L 2/0047* (2013.01); *A61L 27/3683* (2013.01); *C07K 14/78* (2013.01)

(58) Field of Classification Search
CPC .............. A61L 27/3633; A61L 2/0047; A61L 27/3683; A61L 27/24; C07K 14/78; A61K 38/00
See application file for complete search history.

(56) References Cited

U.S. PATENT DOCUMENTS

| | | |
|---|---|---|
| 3,949,073 A | 4/1976 | Daniels et al. |
| 4,233,360 A | 11/1980 | Luck et al. |
| 4,439,521 A | 3/1984 | Archer et al. |
| 4,544,516 A | 10/1985 | Hughes et al. |
| 4,582,640 A | 4/1986 | Smestad et al. |
| 4,600,533 A | 7/1986 | Chu et al. |
| 4,703,108 A | 10/1987 | Silver |
| 4,743,552 A | 5/1988 | Friedman et al. |
| 4,776,853 A | 10/1988 | Klement et al. |
| 4,789,663 A | 12/1988 | Wallace et al. |
| 4,801,299 A | 1/1989 | Brendel et al. |
| 4,829,000 A | 5/1989 | Kleinman et al. |
| 4,902,508 A | 2/1990 | Badylak et al. |
| 4,912,057 A | 3/1990 | Guirguis et al. |
| 4,956,178 A | 9/1990 | Badylak et al. |
| 5,032,508 A | 7/1991 | Naughton et al. |
| 5,163,955 A | 11/1992 | Love et al. |
| 5,204,382 A | 4/1993 | Wallace et al. |
| 5,266,480 A | 11/1993 | Naughton et al. |
| 5,275,826 A | 1/1994 | Badylak et al. |
| 5,281,422 A | 1/1994 | Badylak et al. |
| 5,336,616 A | 8/1994 | Livesey et al. |
| 5,352,463 A | 10/1994 | Badylak et al. |
| 5,372,821 A | 12/1994 | Badylak et al. |
| 5,420,248 A | 5/1995 | Devictor et al. |
| 5,460,962 A | 10/1995 | Kemp et al. |
| 5,478,739 A | 12/1995 | Sivka et al. |
| 5,518,915 A | 5/1996 | Naughton et al. |
| 5,554,389 A | 9/1996 | Badylak et al. |
| 5,604,106 A | 2/1997 | Liotta et al. |
| 5,641,518 A | 6/1997 | Badylak et al. |
| 5,695,998 A | 12/1997 | Demeter et al. |
| 5,753,267 A | 5/1998 | Badylak et al. |
| 5,863,531 A | 1/1999 | Naughton et al. |
| 5,866,414 A | 2/1999 | Badylak et al. |
| 5,885,619 A | 3/1999 | Patel et al. |
| 5,948,429 A | 9/1999 | Bell et al. |
| 5,955,110 A | 9/1999 | Patel et al. |
| 6,020,200 A | 2/2000 | Enevold |
| 6,022,743 A | 2/2000 | Naughton et al. |
| 6,087,157 A | 7/2000 | Badylak et al. |
| 6,099,567 A | 8/2000 | Badylak et al. |
| 6,171,344 B1 | 1/2001 | Atala |
| 6,187,039 B1 | 2/2001 | Hiles et al. |
| 6,187,047 B1 | 2/2001 | Kwan et al. |
| 6,206,931 B1 | 3/2001 | Cook et al. |
| 6,241,981 B1 | 6/2001 | Cobb et al. |
| 6,248,587 B1 | 6/2001 | Rodgers et al. |

(Continued)

FOREIGN PATENT DOCUMENTS

| | | |
|---|---|---|
| AU | 48841/99 | 3/2000 |
| CA | 2212704 | 8/1996 |

(Continued)

OTHER PUBLICATIONS

Search Report & Written Opinion issued Int'l Appl. No. PCT/US2018/016069 (2018).
PCT Search Report and Written Opinion prepared for PCT/US2018/016069, completed Mar. 9, 2018.
"Basement Membrane" accessed online at http://en.wikipedia.org/wiki/Basement membrane#Composition on Jun. 11, 2010.
"Extracellular Matrix" accessed at http://en.wikipedia.org/wiki/Extracellular_matrix on Jun. 11, 2010.
Bell, Brett J. et al., "Cell Density and Extracellular Matrix (ECM) Microstructure Control Mechanical Behavior of Engineered Tissue Constructs", *2005 Summer Bioengineering conference*, (Jun. 22-26, 2005).
Bjornsson, S., "Simultaneous Preparation and Quantitation of Proteoglycans by Precipitation with Alcian Blue", Analytical Biochemistry, vol. 210, 1993, pp. 282-291.

(Continued)

*Primary Examiner* — Jessica Worsham
(74) *Attorney, Agent, or Firm* — Barnes & Thornburg LLP

(57) ABSTRACT

The invention relates to methods of preparing matrices, and compositions therefor. In particular, the invention relates to methods of preparing collagen matrices, and compositions therefor, including kits and graft compositions.

19 Claims, 7 Drawing Sheets

(56) References Cited

U.S. PATENT DOCUMENTS

| | | |
|---|---|---|
| 6,264,992 B1 | 7/2001 | Voytik-Harbin et al. |
| 6,358,284 B1 | 3/2002 | Fearnot et al. |
| 6,375,989 B1 | 4/2002 | Badylak et al. |
| 6,379,710 B1 | 4/2002 | Badylak |
| 6,384,196 B1 | 5/2002 | Weis et al. |
| 6,419,920 B1 | 7/2002 | Mineau-Hanschke |
| 6,444,229 B2 | 9/2002 | Voytik-Harbin et al. |
| 6,475,232 B1 | 11/2002 | Babbs et al. |
| 6,485,723 B1 | 11/2002 | Badylak et al. |
| 6,497,875 B1 | 12/2002 | Sorrell et al. |
| 6,576,265 B1 | 6/2003 | Spievack |
| 6,586,493 B1 | 7/2003 | Massia et al. |
| 6,592,623 B1 | 7/2003 | Bowlin et al. |
| 6,592,794 B1 | 7/2003 | Bachrach |
| 6,666,892 B2 | 12/2003 | Hiles et al. |
| 6,682,670 B2 | 1/2004 | Noff |
| 6,793,939 B2 | 9/2004 | Badylak |
| 6,893,812 B2 | 5/2005 | Woltering et al. |
| 6,918,396 B1 | 7/2005 | Badylak et al. |
| 6,962,814 B2 | 11/2005 | Mitchell et al. |
| 7,029,689 B2 | 4/2006 | Berglund et al. |
| 7,087,089 B2 | 8/2006 | Patel et al. |
| 7,175,841 B2 | 2/2007 | Badylak et al. |
| 7,338,517 B2 | 3/2008 | Yost et al. |
| 7,771,717 B2 | 8/2010 | Badylak et al. |
| 7,795,022 B2 | 9/2010 | Badylak |
| 7,815,686 B2 | 10/2010 | Badylak |
| 8,084,055 B2 | 12/2011 | Voytik-Harbin et al. |
| 8,222,031 B2 | 7/2012 | Noll |
| 8,241,905 B2 | 8/2012 | Forgacs et al. |
| 8,343,758 B2 | 1/2013 | Cheema et al. |
| 8,431,158 B2 | 4/2013 | Shoseyov |
| 8,449,902 B2 | 5/2013 | Brown et al. |
| 8,512,756 B2 | 8/2013 | Voytik-Harbin et al. |
| 8,518,436 B2 | 8/2013 | Voytik-Harbin et al. |
| 8,580,564 B2 | 11/2013 | Brown et al. |
| 8,652,500 B2 | 2/2014 | Bosley, Jr. |
| 8,741,352 B2 | 6/2014 | Hodde et al. |
| 8,785,389 B2 | 7/2014 | Brown et al. |
| 9,101,693 B2 | 8/2015 | Brown et al. |
| 9,205,403 B2 | 12/2015 | Dubois |
| 9,707,703 B2 | 7/2017 | Tully |
| 9,744,123 B2 | 8/2017 | Castiglione-Dodd et al. |
| 9,757,495 B2 | 9/2017 | Murray |
| 10,314,940 B2 | 6/2019 | Voytik-Harbin |
| 2002/0076816 A1 | 6/2002 | Dai et al. |
| 2002/0170120 A1 | 11/2002 | Eckmayer et al. |
| 2002/0172705 A1 | 11/2002 | Murphy et al. |
| 2003/0113302 A1 | 6/2003 | Revazoa et al. |
| 2003/0216811 A1 | 11/2003 | Badylak |
| 2003/0216812 A1 | 11/2003 | Badylak |
| 2004/0006395 A1 | 1/2004 | Badylak |
| 2004/0030404 A1 | 2/2004 | Noll et al. |
| 2004/0037813 A1 | 2/2004 | Simpson et al. |
| 2004/0078076 A1 | 4/2004 | Badylak et al. |
| 2004/0137616 A1 | 7/2004 | Isseroff et al. |
| 2005/0014181 A1 | 1/2005 | Galis et al. |
| 2005/0019419 A1 | 1/2005 | Badylak et al. |
| 2005/0153442 A1 | 7/2005 | Katz et al. |
| 2005/0202058 A1 | 9/2005 | Hiles |
| 2005/0226856 A1 | 10/2005 | Ahlfors |
| 2005/0260748 A1 | 11/2005 | Chang et al. |
| 2005/0266556 A1 | 12/2005 | Yoder et al. |
| 2006/0014284 A1 | 1/2006 | Graeve |
| 2006/0134072 A1 | 6/2006 | Pedrozo et al. |
| 2006/0147501 A1 | 7/2006 | Hillas et al. |
| 2006/0165667 A1 | 7/2006 | Laughlin et al. |
| 2006/0235511 A1 | 10/2006 | Osborne |
| 2006/0257377 A1 | 11/2006 | Atala et al. |
| 2007/0026518 A1 | 2/2007 | Healy et al. |
| 2007/0077652 A1 | 4/2007 | Peled et al. |
| 2007/0141037 A1 | 6/2007 | Badylak et al. |
| 2007/0190646 A1 | 8/2007 | Engler et al. |
| 2007/0269476 A1 | 11/2007 | Voytik-Harbin et al. |
| 2008/0025956 A1 | 1/2008 | Yoder et al. |
| 2008/0070304 A1 | 3/2008 | Forgacs et al. |
| 2008/0095815 A1 | 4/2008 | Mao |
| 2008/0107750 A1 | 5/2008 | Hodde et al. |
| 2008/0181935 A1 | 7/2008 | Bhatia et al. |
| 2008/0199441 A1 | 8/2008 | Peled |
| 2008/0268052 A1 | 10/2008 | Voytik-Harbin et al. |
| 2009/0011021 A1 | 1/2009 | Voytik-Harbin et al. |
| 2009/0069893 A1 | 3/2009 | Paukshto et al. |
| 2009/0175922 A1 | 7/2009 | Voytik-Harbin et al. |
| 2009/0269386 A1 | 10/2009 | Zubery et al. |
| 2009/0280180 A1 | 11/2009 | Voytik-Harbin et al. |
| 2009/0324681 A1 | 12/2009 | Badylak |
| 2010/0119578 A1 | 5/2010 | To et al. |
| 2010/0143476 A1 | 6/2010 | March et al. |
| 2010/0272697 A1 | 10/2010 | Naji et al. |
| 2011/0182962 A1 | 7/2011 | McKay |
| 2012/0273993 A1 | 1/2012 | Shoseyov |
| 2012/0027732 A1 | 2/2012 | Voytik-Harbin et al. |
| 2012/0094376 A1 | 4/2012 | Voytik-Harbin et al. |
| 2012/0115222 A1 | 5/2012 | Voytik-Harbin et al. |
| 2012/0141417 A1 | 5/2012 | Voytik-Harbin et al. |
| 2012/0171768 A1 | 7/2012 | Voytik-Harbin et al. |
| 2012/0189588 A1 | 7/2012 | Nahas et al. |
| 2012/0297550 A1 | 11/2012 | Ngo et al. |
| 2014/0056865 A1 | 2/2014 | Samaniego |
| 2014/0193473 A1 | 7/2014 | Yoder et al. |
| 2014/0193477 A1 | 7/2014 | Chaikof et al. |
| 2015/0105323 A1 | 4/2015 | Novak et al. |
| 2015/0367030 A1 | 12/2015 | Murray |
| 2016/0175482 A1 | 6/2016 | Quirk et al. |
| 2018/0050130 A1 | 2/2018 | Jiang et al. |
| 2018/0127719 A1 | 5/2018 | Nahas et al. |
| 2019/0351097 A1 | 11/2019 | Voytik-Harbin |

FOREIGN PATENT DOCUMENTS

| | | |
|---|---|---|
| DE | 201 15 753 | 1/2002 |
| EP | 0443094 | 8/1991 |
| EP | 1264878 | 12/2002 |
| EP | 1 270 672 A1 | 1/2003 |
| EP | 1 674 116 A2 | 6/2006 |
| GB | 2366736 | 3/2002 |
| JP | 1-247082 | 10/1989 |
| JP | 6-510927 | 12/1994 |
| JP | 7-74239 | 8/1995 |
| JP | 07 074239 B | 8/1995 |
| WO | 92/15676 | 9/1992 |
| WO | 93/00441 | 1/1993 |
| WO | 93/05798 | 4/1993 |
| WO | WO 94/03119 | 2/1994 |
| WO | 94/11008 | 5/1994 |
| WO | 94/23016 | 10/1994 |
| WO | 96/24661 | 8/1996 |
| WO | 97/17038 | 5/1997 |
| WO | 98/06445 | 2/1998 |
| WO | 98/25637 | 6/1998 |
| WO | 98/52637 | 11/1998 |
| WO | 00/15765 | 3/2000 |
| WO | 00/62833 | 10/2000 |
| WO | 01/10355 | 2/2001 |
| WO | WO 2001/023529 | 4/2001 |
| WO | 01/45765 | 6/2001 |
| WO | WO 2001/045765 | 6/2001 |
| WO | 01/48153 | 7/2001 |
| WO | 01/78754 | 10/2001 |
| WO | 02/07646 | 1/2002 |
| WO | 02/14480 | 2/2002 |
| WO | 02/20729 | 3/2002 |
| WO | 2002/102237 | 12/2002 |
| WO | 2003/068287 | 8/2003 |
| WO | 2003/071991 | 9/2003 |
| WO | 03/087337 | 10/2003 |
| WO | 03/092471 | 11/2003 |
| WO | 03/097694 | 11/2003 |
| WO | WO 04/028404 | 4/2004 |
| WO | 2004/060426 | 7/2004 |
| WO | WO 04/078120 | 9/2004 |
| WO | 2006/003442 | 1/2006 |
| WO | 2006/124946 | 11/2006 |

(56) References Cited

FOREIGN PATENT DOCUMENTS

| WO | WO 2006/125025 | 11/2006 |
|---|---|---|
| WO | WO 2007/028079 | 3/2007 |
| WO | WO 2007/136634 | 11/2007 |
| WO | WO 2008/036393 | 3/2008 |
| WO | 00/47219 | 8/2008 |
| WO | 2008/124169 | 10/2008 |
| WO | WO 2009/076441 | 6/2009 |
| WO | WO 2010/123928 | 10/2010 |
| WO | WO 2011/009054 | 1/2011 |
| WO | 2012/004564 | 1/2012 |
| WO | 2017/044847 | 3/2017 |
| WO | 2018/144496 | 8/2018 |
| WO | WO 2019/023266 A1 | 1/2019 |

OTHER PUBLICATIONS

Brennan and Davison, "Role of aldehydes in collagen fibrillogenesis in vitro," Biopolymers, vol. 19, 1980, Issue 10, p. 1861-1873.
Brightman et al., "Time-Lapse Confocal Reflection Microscopy of Collagen Fibrillogenesis and Extracellular Matrix Assembly In Vitro", *Biopolymers*, vol. 54, 222-234, (2000).
Callister, W. D, Jr., Materials Science and Engineering: an Introduction, 3$^{rd}$ edition, New York, NY, John Wiley & Sons, Inc., 1994.
Chandrakasan et al. J. Biol. Chem., 1976, 251:6062-67.
Ciovacco et al., Bone, 2009, 44(1):80-86.
Comper, W. D., and A. Veis, "Characterization of Nuclei in in Vitro Collagen Fibril Formation", Biopolymers, vol. 16, 1977, pp. 2133-2142.
Compston, "Bone marrow and bone: a functional unit," Journal of Endocrinology, 173: 387-394, 2002.
Davis, et al., "Injectable Self-Assembling Peptide Nanofibers Create Intramyocardial Microenvironments for Endothelial Cells", *Circulation*, 111, 442-50, (Feb. 1, 2005).
Fulzele, S. V., P. M. Satturwar, A. K. Dorle, "Study of the Biodegradation and in Vivo Biocompatibility of Novel Biomaterials", European Journal of Pharmaceutical Sciences, vol. 20, 2003, pp. 53-61.
Gallop, P. M., and S. Seifter, "Preparation and Properties of Soluble Collagens", Soluble Collagens, 1963, pp. 635-641.
Gelman et al., "Collagen Fibril Formation in Vitro," J. Biol. Chem., 1979, 254(22): 11741-11745.
Gelman et al., "Collagen Fibril Formation," J. Biol. Chem., 1979, 254(1):180-186.
Griffey, S., N. D. Schwade, C. G. Wright, "Particulate Dermal Matrix as an Injectable Soft Tissue Replacement Material", J. Biomed. Mater. Res. vol. 58, 2001, pp. 10-15.
Hou, et al., "Radiolabeled Cell Distribution After Intramyocardial, Intracoronary, and Interstitial Retrograde Coronary Venous Delivery", *Circulation*, 112, 150-6, (Aug. 30, 2005).
Hunt, T. K., P. Twomey, B. Zederfeldt, and J. E. Dunphy, "Respiratory Gas Tensions and PH in Healing Wounds", American Journal of Surgery, vol. 114, 1967, pp. 302-307.
Ingram, D. A., et al., "Identification of a Novel Hierarchy of Endothelial Progenitor Cells Using Human Peripheral and Umbilical Cord Blood", Blood, 104, 2752-2760, (2004).
Boder, G.B., "Mammalian Cell Cultures for Genetically Engineered Products," Toxicologic Pathology, 1989, 17(4) p. 827.
Delcourt-Huard, et al., "Reconstituted Human Gingivial Epithelium: Nonsubmerged In Vitro Model," In Vitro Cellular & Developmental Biology Animal, Jan. 1997, 33(1) p. 30-6.
International Search Report for International Application No. PCT/US07/020463, Feb. 21, 2008, 6 pgs.
International Search Report/Written Opinion for PCT/US2007/011681 completed Nov. 6, 2007.
Kacena et al., J. of Histotechnology, 2004, 27:119-130.
Knott et al., "Collagen Cross-Links in Mineralizing Tissues: A Review of Their Chemistry, Function, and Clinical Relevance," 1998, 22(3):181-187.

Kondo et al., "Biology of Hematopoietic Stem Cells and Progenitors: Implications for Clinical Application," Annu. Rev. Immunol., 2003, 21:759-806.
Korff et al., Jour. of Cell Science, vol. 112: 3249-3258 (1999).
Kreger et al., "Hyaluronan concentration within a 3D collagen matrix modulates matrix viscoelasticity, but not fibroblast response," Matrix Biol., 2009, 28(6):336-46.
Kreger, "Design of 3D Collagen Matrices for Cell Delivery and Guidance in Tissue Engineering," Thesis Submitted to the Faculty of Purdue University in Partial Fulfillment of the Requirements for the Degree of Doctor of Philosophy, May 2009, Purdue University.
Lin et al., "Comparison of Physical-Chemistry Properties of Type I Collagen from Different Species," *Food Chemistry*, 99(2): 244-251 (2005).
Malvern, Introduction to the Mechanics of a Continuous Medium. Upper Saddle River, NJ: Prentice-Hall, 1969.
Marotta, M., G. Martino, "Sensitive Spectrophotometric Method for the Quantitative Estimation of Collagen", Analytical Biochemistry, vol. 150, 1985, pp. 86-90.
Miller et al., "Preparation and Characterization of the Different Types of Collagen," *Methods in Enzymology*, 82: 33-64 (1982).
Miller, E. J., E. H. Epstein, Jr., and K. A. Piez, "Identification of Three Genetically Distinct Collagens by Cyanogen Bromide Cleavage of Insoluble Human Skin and Cartilage Collagen", Biochemical and Biophysical Research Communications, vol. 42, No. 6, 1971, pp. 1024-1029.
Na, "Monomer and Oligomer of Type I Collagen: Molecular Properties and Fibril Assembly," *Biochemistry*, 1989, 28(18):7161-7167.
Narmoneva et al., "Endothelial Cells Promote Cardiac Myocyte Survival and Spatial Reorganization", *Circulation*, 110, 962-968, (Aug. 24, 2004).
Nguyen et al., "Comparison of the Amino Acid Composition of Two Commercial Porcine Skins (Rind)," *Journal of Agricultural and Food Chemistry*, 34(3): 565-572 (1986).
Nielsen, T. B. and J. A. Reynolds, "Measurements of Molecular Weights by Gel Electrophoresis", Methods in Enzymology, vol. 48, Hirs and Temasheff, Eds., Academic Press, New York, 1978, pp. 3-10.
Orschell-Traycoff et al., Blood, 2000, 96:1380-1387.
Osborne, et al., "Investigation into the tensile properties of collagen/chondroitin-6-sulphate gels: the effect of crosslinking agents and diamines", *Medical & Biological Engineering & Computing*, vol. 36, 129-134, (1998).
Ozerdem, et al., "Physical Response of Collagen Gels to Tensile Strain", *Journal of Biomechanical Engineering*, vol. 117, 397-401, (Nov. 1995).
Pizzo et al., "Cell-Extracellular Matrix (ECM) Micro-Mechanical Behavior Depends on ECM Microstructure and Cell Type", *2005 Summer Bioengineering Conference*, (Jun. 22-26, 2005).
Pizzo et al., "Extracellular matrix (ECM) microstructural composition regulates local cell-ECM biomechanics and fundamental fibroblast behaviour: a multidimensional perspective", *J Appl Physiol*, 98: 1909-1921, (2005).
Pizzo et al., "Long-term Production of Choline Acetylatransferase in the CNS After Transplantation of Fibroblasts Modified with a Regulatable Vector", *Mol Brain Res*, 126, 1-13 (2004).
Rehman, et al., "Secretion of Angiogenic and Antiapoptotic Factors by Human Adipose Stromal Cells", *Circulation*, 109: 1292-8, (Mar. 16, 2004).
Reinlib, et al., "Cell Transplantation as Future Therapy for Cardiovascular Disease?", *Circulation*, 101: e182-e187, (2000).
Roeder B. A., K. Kokini, J. E. Sturgis, J. P. Robinson, S. L. Voytik-Harbin, "Tensile Mechanical Properties of Three-Dimensional Type I Collagen Extracellular Matrices with Varied Microstructure", J. Biomech. Eng., vol. 124, 2002, pp. 214-222.
Roeder et al., "Local, Three-Dimensional Strain Measurements Within Largely Deformed Extracellular Matrix Constructs", *J Biomech Eng*, 126, 699-708, (2004).
Scadden, "The stem cell niche as an entity of action," Nature, 441: 1075-1079, 2006.
Schechner et al., "In vivo formation of complex microvessels lined by human endothelial cells in an immunodeficient mouse," PNAS, Aug. 1, 2000, vol. 97, No. 16, 9191-9196.

(56) References Cited

OTHER PUBLICATIONS

Schilling, J. A., W. Joel, H. M. Shurley, "Wound Healing: A Comparative Study of the Histochemical Changes in Granulation Tissue Contained in Stainless Steel Wire Mesh and Polyvinyl Sponge Cylinders", Surgery, vol. 46, No. 4, Oct. 1959, pp. 702-710.
Shiozawa et al., "The bone marrow niche: habitat to hematopoietic and mesenchymal stem cells, and unwitting host to molecular parasites," Leukemia, 22(5): 941-950, 2008.
Sieminski et al., Expt. Cell Res., vol. 297, pp. 574-584 (2004).
Spradling et al., "Stem Cells Find Their Niche," Nature, 414: 98-104, 2001.
Strang, et al., *Linear Algebra and Its Applications*. 3rd edition. San Diego, CA: Academic Press, 1988.
Sykes, B., B. Puddle, M. Francis, and R. Smith, "The Estimation of Two Collagens from Human Dermis by Interrupted Gel Electrophoresis", Biochemical and Biophysical Research Communications, vol. 72, No. 4, 1976, pp. 1472-1480.
Veis, Arthur, et al., "Fundamentals of Interstitial; Collagen Self-Assembly", 1994, Extracellular Matrix Assembly and Structure, Academic Press, pp. 15-45.
Voytik-Harbin et al., "Application and Evaluation of the Alamarblue Assay for Cell Growth and Survival of Fibroblasts", *In Vitro Cell Dev Biol Anim*, 34, 239-246, (1998).
Voytik-Harbin et al., "Simultaneous Mechanical Loading and Confocal Reflection Microscopy for Three-Dimensional Microbiomechanical Analysis of Biomaterials and Tissue Constructs", *Microsc Microanal*, 9, 74-85, (2003).
Voytik-Harbin et al., Small Intestinal Submucosa: A Tissue-Derived Extracellular Matrix That Promotes Tissue-Specific Growth and Differentiation of Cells in Vitro, *Tissue Engineering*, 4, 2, 157-174, (1998).
Voytik-Harbin et al., "Three-Dimensional Imaging of Extracellular Matrix and Extracellular Matrix-Cell Interactions", *Methods in Cell Biology*, 63, 583-597, (2001).
Wess, Collagen fibrillar structure and hierarchies in P. Fratzl (ed.), Collagen: Structure and Mechanics, Springer Science + Business Media, LLC, New York, 2008, 53-60.
Yoder et al., "Redefining endothelial progenitor cells via clonal analysis and hematopoietic stem/progenitor cell principals," *BLOOD*, 2007, 109:1801-1809.
International Search Report and Written Opinion for PCT/US2008/086232, Jan. 16, 2009, 12 pages.
Bailey JL et al., "Collagen Oligomers Modulate Physical and Biological Properties of Three-Dimensional Self-Assembled Matrices," Biopolymers, 2010; 95(2): 77-93.
Na et al., "In Vitro Collagen Fibril Assembly in Glycerol Solution: Evidence for a Helical Cooperative Mechanism Involving Microfibrils," Biochemistry, 1986; 25: 958-966.
Na et al., "Mechanism of in Vitro Collagen Fibril Assembly," Journal of Biological Chemistry, 1986; 261(26): 12290-12299.
Voytik-Harbin et al., "Identification of Extractable Growth Factors from Small Intestine Submucosa," J Cell. Biochemistry, 1997; 67: 478-491.
Condell RA et al., "Analysis of Native Collagen Monomers and Oligomers by Size-Exclusion High-Performance Liquid Chromatography and its Application," *Analytical Biochemistry*, 1993; 212: 436-445.
"Density" from Merriam-Webster online, accessed on Feb. 1, 2011.
Brandner et al., "Replicating the Hematopoietic Stem Cell Niche," Purdue University, BME Graduate Student Association Research Symposium, Poster Presentation, Jul. 16, 2009.
Whittington et al., "Collagen oligomers modulate physical and cell-instructive properties of polymerizable collagen matrices," Biomaterials Day Society for Biomaterials, Nov. 6, 2010 (PowerPoint presentation and poster).
Kreger et al., "Polymerization and matrix physical properties as important design considerations for soluble collagen formulations," 2010, Biopolymers, 93(8): 690-707.

Critser et al., "Collagen matrix physical properties modulate endothelial colony forming cell-derived vessels in vivo," 2010, Microvasc. Res., 80(1): 23-30.
Munakata, et al., Glycobiology, vol. 9, 1023-1027 (1999).
Kim, "Characterization of Acid-soluble Collagen from Pacific Whiting Surimi Processing Byproducts," J. Food Science, 2004, 69: C637-C642.
Billiar, Cellular and Biomolecular Mechanics and Mechanobiology, Amit Gefen, Ed., p. 210 (2011).
Ho et al., "Characterization of Collagen Isolation and Application of Collagen Gel as a Drug Carrier", J. of Controlled Release, vol. 44, pp. 103-112 (1997).
Liu, Asian-Aust J. Anim. Sci, 2001; 14(11):1638-1644.
Lynn et al., "Antigenicity and immunogenicity of collagen," J Biomed Mater Res, Part B: Appl Biomater, 2004; 71B: 343-354.
Taichman et al., "Human Osteoblasts Support Hematopoiesis through the Production of Granulocyte Colony-stimulating Factor," Journal of Experimental Medicine, 1994; 179:1677-1682.
TeBmar et al., "Hydrogels for tissue engineering," *Fundamentals of Tissue Engineering and Regenerative Medicine*, 2009; p. 495-517.
Koken, "About Collagen," Technical information, Support webpage, 2006.
Taqvi et al., "Influence of scaffold physical properties and stromal cell coculture on hematopoietic differentiation of mouse embryonic stem cells," *Biomaterials*, 2006; 24:6024-6031.
Engler et al., "Matrix elasticity directs stem cell lineage specification," *Cell*, 2006; 126:677-689.
Young, et al., "Adult Stem Cells." Anat. Record Pt. A: Disc. Mol. Cell. Evol. Biol. 276A:75-102 (2004).
Yang, et al., "The application of recombinant human collagen in tissue engineering." *Biodrugs* 18:103-119 (2004).
Fischbach, et al., "Three-dimensional in vitro model of adipogenesis: coparison of culture conditions." *Tissue Engineering* 10:215-229 (2004).
Reinisch et al, "Humanized large-scale expanded endothelial colony-forming cells function in vitro and in vivo," *Blood*, 2009; 113:6716-6725.
Silver et al., "Collagen self-assembly and the development of tendon mechanical properties," *Journal of Biomechanics*, 2003; 36:1529-1553.
Product information: Collagen Solution—Type I from rat tail, Sigma, http://www.sigmaaldrich.com/etc/medialib/docs/Sigma/Datasheet/3/c3867dat.Par.0001.File.tmp/c3867dat.pdf.
Gallagher D, "Stem cells being made from blood," available at www.bbc.co.uk/news/health-20539835.
Ingram D et al., "Vessel wall-derived endothelial cells rapidly proliferate because they contain a complete hierarchy of endothelial progenitor cells," *Blood*, 2005; 105(7):2783-6 (Epub Dec. 7, 2004).
Ingram D et al., "Unresolved questions, changing definitions, and novel paradigms for defining endothelial progenitor cells via clonal analysis and hematopoietic stem/progenitor cell principals," *Blood*, 2007; 109(5):1801-9 (Epub Oct. 19, 2006).
Prater DN et al., "Working hypothesis to redefine endothelial progenitor cells," *Leukemia*, 2007; 21(6):1141-9 (Epub Mar. 29, 2007).
Case J et al., "Human CD34+AC133+VEGFR-2+ cells are not endothelial progenitor cells but distinct, primitive hematopoietic progenitors," *Exp Hematol.*, 2007; 35(7):1109-18.
Hirschi KK et al, "Assessing identify, phenotype, and fate of endothelial progenitor cells," *Arterioscler Thromb Vasc Biol*, 2008; 28(9):1584-95 (Epub Jul. 31, 2008).
Timmermans F et al., "Endothelial progenitor cells: identify defined?", *J Cell Mol Med*, 2009; 13(1):87-102.
Mund JA et al, "Endothelial progenitor cells and cardiovascular cell-based therapies," *Cytotherapy*, 2009; 11(2):103-13.
Chor Wing Tam et al. EWMA Journal, 2012; 12(2).
Boyd et al. Atlas and Text of Corneal Pathology and Surgery; 2011 [Document REJECTED by EXAM. because illegible].
Stem Cell Differentiation (science and global issues/biology, cell biology), 2013.
Shimizu, "Fabrication of pulsatile cardiac tissue grafts using a novel 3-dimensional cell sheet manipulation technique and temperature-responsive cell culture surfaces," Circ Res., 2002, 90:e40-48.

(56) References Cited

OTHER PUBLICATIONS

Mizuno et al., "Osteogenesis by bone marrow stromal cells maintained on type 1 collagen matrix gels in vivo." Bone 20:101-107 (1997).
Young et al., "Use of meschymal stem cells in a collagen matrix for Achilles tendon repair." J. Ortopaedic Res. 16 406-413 (1998).
Vasiliev and Gelfand, Neoplastic and Normal Cells in Culture, Cambring University Press, p. 19, 1981.
"Stem Cells and the future of Regenerative Medicine" published by National Academy of Sciences, p. 19, 2002.
McBeath et al., "Cell shape, cytoskeletal tension, and RhoA regulate stem cell lineage commitment," *Developmental Cell*, 2004; 6:483-495.
Engler et al., "Myotubes differentiate optimally on substrates with tissue-like stiffness: pathological implications for soft or stiff microenvironments," *Journal of Cell Biology*, 2004; 165:877-887.
Kong et al., "FRET measurements of cell-traction forces and nano-scale clustering of adhesion ligands varied by substrate stiffness," *PNAS*, 2005; 102:4300-4305.
Settleman, "Tension Precedes Commitment—Even for a Stem Cell," *Molecular Cell*, 2004; 14:148-150.
Engler et al., "Substrate elasticity directs adult mesenchymal stem cell differentiation," Abstract 783, The 37th Middle Atlantic Regional Meeting, May 2005.
Wang et al, Sheng Li Xue Bao, 2005, 57(2): 259-269; Astract Only.
Williams et al, 1978, Journ Biol Chem, 253: 6578-6585.
Huang et al, 2005, Mechanisms and Dynamics of Mechanical Strengthening in Ligament-Equivalent Fibroblast-Populated Collagen Matrices, Annals of Biomedical Engineering, 21: 289-305.
Rucha Joshi: "Purdue e-Pubs Open Access Dissertations Theses and Dissertations Designer Collagen-Fibril Biograft Materials for Tunable Molecular Delivery," Jan. 1, 2016 https://docs.lib.purdue.edu/open_access_dissertations/1218.
"Artificial Blood Vessel," English translation of Japanese Patent Application Publication No. 3-12169, 1991, 16 pages.
Asem, E.K. et al. "Basal lamina of Avian Ovarian Follicle: Influence on Morphology of Granulosa Cells In-Vitro," Comparative Biochemistry and Physiology, Part C, 125 (2000), pp. 189-201.
Blay et al., "Epidermal Growth Factor Promotes the Chemotactic Migration of Cultured Rat Intestinal Epithelial Cells," J. Cell Physiology, 1985, 124(1) pp. 107-112.
Asem, E.K. et al. "Effect of Basal Lamina on Progesterone Production by Chicken Granulosa Cells In Vitro—Influence of Follicular Development," Comparative Biochemistry and Physiology, Part C, 125 (2000) pp. 233-244.
Campbell, J.H. et al. "Endothelial Cell Influences on Vascular Smooth Muscle Phenotype," Ann. Rev. Physiol., 1986, vol. 48, 384-91.
Nugent, H.M et al. "Endothelial Implants inhibit Intimal Hyperplasia After Porcine Angioplasty," Circulation Research, Mar. 5, 1999, 84(4) pp. 384-391.
Hirschi, K.K. et al. "PDGF, TGF-β, and Heterotypic Cell-Cell Interactions Mediate Endothelial Cell-Induced Recruitment of 10T1/2 Cells and Their Differentiation to a Smooth Muscle Fate," The Journal of Cell Biology, 1998, 141(3) pp. 805-814.
Grinnel, "Cell-Collagen Interactions: Overview," Methods in Enzymology, 1982, 82, 499-5.
Badylak, S.T., et al. "Endothelial Cell Adherence to Small Intestinal Submucosa: An Acellular Bioscaffold," Biomaterials, 1999, 20, pp. 2257-2263.
Mikos, A.G., et al., "Islet Transplantation to Create a Bioartificial Pancreas," Biotech. and Bioengineering, 1994, 43, 673-7.
Bell, et al., "Production of a tissue-like structure by contraction of collagen lattices by human fibroblasts of different proliferative potential in vitro," Mar. 1979, Proc. Natl. Sci. USA, 76(3) pp. 1274-1278.
Bhatia, S.N. et al., "Controlling Cell Interactions by Micropatterning in Co-Cultures: Hepatocytes and 3T3 Fibroblasts," Journal of Biomedical Materials Research, 1997, 34, pp. 189-199.

Sato et al., "Artificial Esophagus," Materials Science Forum, 1997, 250, 105-14.
Schor et al., "The Use of Three-Dimensional Collagen Gels for the Study of Tumour Cell Invasion In Vitro: Experimental Parameters Influencing Cell Migration Into the Gel Matrix," Int. J. Cancer, 1982, 29, 57-62.
Abou-Neel et al. "Use of multiple unconfined compression for fine control of collagen gel scaffold and mechanical properties," Soft Matter, 2006, 2, 986-92.
Boder, G.B. and Hull, R.H., "Introduction to Techniques in Mammalian Cell Culture," Manual of Industrial Microbiology and Biotechnology, 1983, Ed. A.L. Demain and N.A. Solomon, pp. 248-262.
International Preliminary Report on Patentability and Written Report for PCT/US2006/018998; 9 pages.
International Preliminary Report on Patentability and Written Report for PCT/US2006/019130; 8 pages.
International Search Report and Written Opinion for PCT/US2010/042290; 13 pages.
International Search Report and Written Opinion for PCT/US2012/040737; 6 pages.
Castano, E., et al., "Inhibition of DNA Synthesis by Aspirin in Swiss 3T3 Fibroblasts," Journal of Pharmacology and Experimental Therapeutics, 1997, 280(1) p. 366-72.
International Search Report and Written Opinion for PCT/US2015/047176; 12 pages.
Deluca, et al., "Evidence That Human Oral Epithelium Reconstituted In Vitro and Transplanted on Patients with Defects in the Oral Mucosa Retains Properties of the Original Donor Site," Transplantation, 1990, 50(3) p. 454-9.
Elsdale and Bard, "Collagen Substrata for Studies on Cell Behavior," The Journal of Cell Biology, 1972, 54, p. 626-37.
Emerman et al., "Maintenance and Induction of Morphological Differentiation in Dissociated Mammary Epithelium on floating Collagen Membranes," In Vitro, 1977, 13(5) pp. 316-328.
Freed et al., "Joint Resurfacing Using Allograft Chondrocytes and Synthetic Biodegradable Polymer Scaffolds," J. Biomedical Materials Res., 1994, 28, p. 891-9.
Freeman et al., "In vivo-like growth of human tumors in vitro," Proc. Natl. Acad. Sci. USA, Apr. 1986, 83, 2694-8.
Freshney, R.I., "Culture of Animal Cells: A Manual of Basic Technique," Chapters 12 and 13, Alan R. Liss, Inc., New York (1994) p. 119-43.
Girasole et al., "17-β Estradiol Inhibits IL-6 Production by Bone Marrow-Derived Stromal Cells and osteoblasts In Vitro: A Potential Mechanism for the Antiosteoporotic Effects of Estrogens," The Journal of Clinical Investigation, Inc. 1992, 89,-. 883-91.
Ho, M., et al., "Identification of Endothelial Cell Genes by Combined Database Mining and Microarray Analysis," Physiol. Genomics, 2003, 13, 249-62.
Ibrahiem, E.I.H., et al. "Orthotopic Implantation of Primary N-[4-(5-Nitro-2-furyl)-2-thiazolyl]formamide-induced Bladder Cancer in Bladder Submucosa: An Animal Model for Bladder Cancer Study," Cancer Research, 1983, 43, 617-20.
Kashtan, H. et al., "Intra-rectal injection of tumor cells: a novel animal model of rectal cancer," Surgical Oncology, 1992, 1, 251-6.
Keyes, K. et al. "An In Vitro Tumor Model: Analysis of Angiogenic Factor Expression after Chemotherapy," Cancer Research, 2002, 62, 5597-602.
Kleinman, et al., "Preparation of Collagen Substrates for Cell Attachment: Effect of Collagen Concentration and Phosphate Buffer," Analytical Biochemistry, 1979, 94, 308-12.
Kleinman, et al., "Membrane Complexes with Biological Activity," Biochemistry, 1986, 25, 312-8.
Kubota, Y. et al., "Role of Laminin and Basement Membrane in the Morphological Differentiation of Human Endothelial Cells into Capillary-like Structures," Journal of Cell Biology, 1988, 107, 1589-98.
Kuo, C.Y., et al., "Formation of Pseudoislets from Human Pancreatic Cultures," Pancreas, 1992, 7(3) 320-5.
Lee, et al., "Modulation of Secreted Proteins of Mouse Mammary Epithelial Cells by the Collagenous Substrata," The Journal of Cell Biology, 1984, 98, 146-55.

(56) References Cited

OTHER PUBLICATIONS

Liu, C. H., et al., "Effects of Salvianolic Acid-A on NIH/3T3 Fibroblast Proliferation, Collagen Synthesis and Gene Expression," World J. Gastroentero, 2000, 6(3) 361-4.

Maru et al., "An Oncogenic Form of the Flt-1 Kinase has a Tubulogenic Potential in a Sinusoidal Endothelial Cell Line," European Journal of Cell Biology, 2000, 79, 130-43.

Michalopoulos & Pitot, "Primary Culture of Parenchymal Liver Cells on Collagen Membranes," Experimental Cell Research, 1975, 94, 70-8.

Mokonjimobe et al., "Hexosaminidase and alkaline phosphatase activities in articular chondrocytes and relationship to cell culture conditions," Experientia, 1992, 48(4) 396-8.

Nerem, R., "Tissue Engineering: The Hope, The Hype and The Future," Tissue Engineering, 2006, 12(5) 1143-50.

Saltzman et al., "Three-dimensional Cell Cultures Mimic Tissues," Ann, N.Y. Acad. Sci., 1992, 665, 259-73.

Shields et al., Invasion of Collagen Gels by Mouse Lympoid Cells, Immunology, 1984, 51, 259-68.

Takahashi, et al., "Compressive force promotes Sox9, type II collagen and aggrecan and inhibits IL-Iβ expression resulting in chondrogenesis in mouse embryonic limb bud mesenchymal cells," Journal of Cell Science, 1998, 111(14) 2067-76.

Vescoi et al., "In vivo-like drug responses of human tumors growing in three-dimensional gel-supported primary culture," Proc. Natl. Acad. Sci. USA, 1987, 84, 5029-33.

Wakitani et al., "Mesenchymal Cell-Based Repair of Large, Full Thickness Defects of Articular Cartilage," J. Bone Joint Surg. Am., Abstract, 1994, 76(4) 579-92.

Yang, E.K. et al., "Tissue Engineered Artificial Skin Composed of Dermis and Epidermis," International Society for Artificial Organs, 2000, 24(1) 7-17.

Friess, "Collagen-biomaterial for drug delivery," European Journal of Pharmaceutics and Biopharmaceutics, 1998, 45(2) 113-36.

Ruszczak et al., "Effect of collagen matrices on dermal wound healing," Advanced drug Delivery Reviews, 2003, 55, 1595-611.

Lillie et al., "Growth of Stratified Squamous Epithelium on Reconstituted Extracellular Matrices: Long-Term Culture," Journal of Investigative Dermatology, 1988, 90(2) 100-9.

Silver et al., "Type I Collagen in Solution," The Journal of Biological Chemistry, 1980, 19(10) 9427-33.

Glowacki, J. and Mizuno, S. "Collagen Scaffolds for Tissue Engineering," Biopolymers, 2007, 89, 338-44.

Sweeney, et al. "Defining the domains of type I collagen involved in heparin-binding and endothelial tube formation," Proceedings of the National Academy of Science, USA 1998, 95, 275-80.

Volpi et al. "On adaptive structures of the collagen fibrils of bone and cartilage," J. Biomech, 24 (Suppl 1), 1991, 67-77, abstract only.

Zhu et al., "Designed composites for mimicking compressive mechanical properties of articular cartilage matrix," Journal of the Mechanical Behavior of Biomedical Materials, 2014, 36, 32-46.

Mienaltowski, et al. "Structure, Physiology, and Biochemistry of Collagens," Advances in Experimental Medicine and Biology, 2014, 802, 5-29.

Whittington, C., et al., "Oligomers Modulate Interfibril Branching and Mass Transport Properties of Collagen Matrices," Microsc Microanal, Oct. 2013, 19(5) 20 pages.

Shoulders, et al., "Collagen Structure and Stability," Annu. Rev. Biochem., 2009, 78, 929-58.

Blum, K.M., et al., "Acellular and high-density, collagen-fibril constructs with suprafibrillar organization," Biomaterials Science, The Royal Society of Chemistry, 2016, 4, 711-23.

Whittington, C.F., et al., "Collagen-Polymer Guidance of Vessel Network Formation and Stabilization by Endothelial Colony Forming Cells In Vitro," Macromolecular Bioscience, 2013, 13, 1135-49.

Brown, et al., "Ultrarapid Engineering of Biomimetic Materials and Tissues: Fabrication of Nano- and Microstructures by Plastic Compression," Advanced Functional Materials, 2005, 15, 1762-70.

Chicatun, et al., "Osteoid-Mimicking Dense Collagen/Chitosen Hybrid Gels," BioMacromolecules, 2011, 12, 2946-56.

Zorlutuna et al., "Nanopatterning of Collagen Scaffolds Improve the Mechanical Properties of Tissue Engineered Vascular Graft," Biomacromolecules, 2009, 10, 814-21.

Caves, et al., "Elastin-linke protein matrix reinforced with collagen microfibers for soft tissue repair," Biomaterials, 2011, 32(23) 5371-9.

Shepard, et al., "Effect of fiber crosslinking on collage-fiber reinforced collagen-chondroitin-6-sulfate materials for regenerating load-bearing soft tissues," Journal of Biomedical Materials Research, 2012, 101(1) 176-84.

Hambli et al., "Physically based 3D finite element model of a single mineralized collagen microfibril," Journal of Theoretical Biology, 2012, 301, 28-41.

Ji et al., "Mechanics of electrospun collagen and hydroxyapatite/collagen nanofibers," Journal of the Mechanical behavior of Biomedical Materials, 2012, 13, 185-93.

Grover, et al., "Crosslinking and composition influence the surface properties, mechanical stiffness and cell reactivity of collagen-based films," Acta Biomater, 2012, 8(8) 3080-90.

Brookes, S. et al., "Three-dimensional tissue-engineered skeletal muscle for laryngeal reconstruction: 3D Tissue Engineered Skeletal Muscle," The Laryngoscope, Aug. 26, 2017, 128(3) 603-9.

Wikipedia, "Oligomer," Sep. 25, 2015, retrieved on Jun. 22, 2018, from https://en.wikipedia.org/w/index.php?title+Oligomer&oldid=682674890.

Wu et al., "Bioprinting three-dimensional cell-laden tissue constructs with controllable degradation," Scientific Reports, 6:24474, Apr. 19, 2016.

Fogolia, et al. "A new method for the preparation of biocompatible silica coated-collagen hydrogels," J. Mater. Chem. B., 2013, vol. 1, pp. 1283-1290.

Stephens, et al, "Oligomeric collagen as an encapsulation material for islet/beta-cell replacement: effect of islet source, dose, implant site, and administration format," Am. J. Physiol. Endocrinol. Metab., 2020, vol. 319, pp. E388-E400.

Brasack, et al. "Biocompatibility of Modified Silica-Protein Composite Layers," Journal of Sol-Gel Science and Technology, 2000, vol. 19, pp. 479-482.

Xi, et al. "Pore size and pore-size distribution control of porous silica," Sensors and Actuators, 1995, vol. B 24-25, pp. 347-352.

Wilson, et al. "A fibril-reinforced poroviscoelastic swelling model for articular cartilage," Journal of biomechanics, 2005, 38(6) pp. 1195-1204.

JPK Instruments, "Collagen: levels of structure and alignment," pp. 1-6, retrieved from the internet 127/2022. https://www.jpk.com/app=technotes-img/AFM/pdf/jpk-app-collagen.14-1.pdf (Year: 2022).

"Polymerization and Matrix Physical Properties as Important Design Considerations for Soluble Collagen Formulations," by S.T. Kreger et al.; Bioploymers, vol. 93 / No. 8; Published Mar. 16, 2010 (18 pages).

Boder G.B. et al. "Long-Term Production of Insulin by Isolated Rabbit Pancreatic Islets in Suspension Culture," J. Cell Biol. 1968, 39(16a).

Backer, M.P., et al. "Large Scale Production of Monoclonal Antibodies in Suspension Culture," Biotechnology and Bioengineering, 1988, 32, pp. 993-1000.

Badylak, S.T., et al. "Directed Connective Tissue Remodeling, Upon a Biologic Collagen Substrate," J. Cell Biochem. 1992, Supplement 16F, Abstract No. CE 027, p. 124.

Bioartificial Organs, Richard Skalak and Fred Fox, eds. Tissue Engineering, Chapter V. Transplants and Artificial Organs, pp. 209, 211-39, and 241-2 (Alan R. Liss, Inc. 1988).

Block, S., "Peroxygen Compounds," Disinfection, Sterilization and Preservation, 4th Edition 1991, pp. 167-181, Phildelphia, Lea, & Febiger.

Boder, G.B., et al. "Visible Light Inhibits Growth of Chinese Hamster Ovary Cells," European J. Cell Biol., 1983, 31, pp. 132-6.

Boder G.B., et al. "Extended Production of Insulin by Isolated Rabbit Pancreatic Islets; Evidence for Biosynthesis of Insulin," Proc. Soc. Exptl. Biol. Med., 1969, 131, p. 507-13.

Boder, G.B., et al. "Long Term Monolayer Cultures of Islet Cells from Neonatal Mice," J. Cell Biol., 1973, 59, p. 29a.

(56) References Cited

OTHER PUBLICATIONS

Denton, G.W., "Chlorhexidine," Disinfection, Sterilization and Preservation, 4th Edition 1991, Philadelphia, Lea, & Febiger, p. 274-89.
Junnosuke, "Tissue culture-Basics and Applications-," Asakura Publishing Co., Ltd., 1965, p. 31.
Kuo C.Y., et al., "Biohybrid Islet-Gland Equivalent for Transplantation," Journal of Cellular Biochemistry, Supplement 18C PZ110, Feb. 13-26, 1994.
Larsson, L. et al., "Changes in the Islets of Langerhans in the Obese Zucker Rat," Lab. Invest. 1977, 36, 593-8.
Francis, et al. "Endothelial cell-matrix interactions in neovascularization," Tissue Engineering Part B: Reviews, 2008, 14(1) 19-32.
Mitra, et al., "Preparation and characterization of malonic acid cross-linked chitosan and collagen 3D scaffolds: an approach on non-covalent interactions," J. Mater. Sci. Mater Med, 2012, 23, 1309-21.
Kuo Ching Chao et al., "A Novel Human Stem Cell Coculture System that Maintains the Survival and Function of Culture Islet-Like Cell Clusters," Cell Transplantation, Jun. 1, 2008, 657-64.

METHODS AND COMPOSITIONS FOR MATRIX PREPARATION

CROSS-REFERENCE TO RELATED APPLICATIONS

This application is a national stage entry under 35 USC § 371 of PCT International Application Number PCT/US2018/016069, filed Jan. 31, 2018, which claims priority under 35 U.S.C. § 119(e) to U.S. Provisional Application Ser. No. 62/452,564 filed on Jan. 31, 2017, the entire disclosures of which are incorporated herein by reference.

FIELD OF THE DISCLOSURE

This invention relates to methods of preparing matrices, and compositions therefor. In particular, the invention relates to methods of preparing collagen matrices, and compositions therefor, including kits and graft compositions.

BACKGROUND AND SUMMARY

The extracellular matrix plays a crucial role in the function of tissues and organs, such as communication between cells, differentiation during embryogenesis, wound healing, adhesion, and cell migration and proliferation. Extracellular matrix graft constructs obtained from natural sources or made synthetically can be used as tissue graft compositions, in both solid and injectable forms, for remodeling tissues in vivo or for in vitro applications, such as for research purposes. The principal component of the extracellular matrix is collagen. Some solubilized collagen compositions, including purified collagen compositions, have matrix-forming capability and can also be used as tissue graft compositions, in both solid and injectable forms, for remodeling tissues in vivo or for in vitro uses. In fact, such collagen-based matrices have broad spanning research and medical applications, including wound and hemostatic dressings, use as surgical implants, substrates for tissue engineered medical products, delivery vehicles for therapeutic cells or molecules, and as three-dimensional in-vitro tissue systems for basic research, including drug development and toxicity testing.

To ensure a high level of manufacturing consistency of collagen-based matrices and low lot-to-lot variability in the functional properties of collagen for use in making collagen-based matrices for both medical and research applications, standardized procedures and reagents are needed for induction of collagen self-assembly and for customization of collagen-based matrices.

Accordingly, the inventors have developed a robust method with a single mixing step for polymerization of collagen, with reagents that mimic physiologic conditions to support supramolecular self-assembly of collagen as observed in the body. In addition, the method and the reagents used in the method described herein are based on physiologic responses such as the viscoelastic properties of self-assembled matrices (for example, shear storage modulus as measured in oscillatory shear and matrix stiffness) as a function of collagen concentration in the polymerization reaction. The methods and compositions described herein produce collagen-based matrices that have properties similar to conventional multi-step polymerization methods involving multiple mixing steps for collagen polymerization including mixing a collagen composition with a buffer solution and then mixing with, for example, with a base such as NaOH to induce polymerization, and then mixing optionally with other reagents. The methods and compositions developed by the inventors have resulted in highly predictable and reproducible in-vitro cell and in-vivo host responses to self-assembled collagen matrices. In another aspect, the inventors have developed methods for sterilizing the collagen, collagen compositions, collagen matrices, collagen solutions, and lyophilized collagen described herein by using ultraviolet radiation, while maintaining polymerization capabilities (e.g., shear storage modulus). The maintenance of polymerization capabilities is contrary to previous studies reporting that ultraviolet radiation negatively affects collagen fibril formation (Mentor et al., Photodermatology, Photoimmunology & Photomedicine, 2001; Miyata et al., Biochem. Biophys. Acta, 1971; Sudoh and Noda, Connect. Tissue Res., 1972). In one embodiment, a method for preparing a matrix is provided. The method comprises polymerizing collagen using a single mixing step comprising mixing a collagen composition with a buffer solution to form a collagen solution, and polymerizing the collagen in the collagen solution to form the matrix.

In another embodiment, a method for preparing a matrix is provided. The method comprises polymerizing collagen by mixing a collagen composition with a buffer solution to form a collagen solution, and polymerizing the collagen in the collagen solution to form the matrix wherein the buffer solution does not contain magnesium ions or manganese ions.

In yet another embodiment, a method for preparing a matrix is provided. The method comprises polymerizing collagen using a single mixing step comprising mixing a collagen composition with a buffer solution to form a collagen solution, wherein the collagen in the collagen solution polymerizes to form the matrix.

In still other embodiments, a collagen matrix prepared according to any of the preceding methods is provided. In yet another embodiment, a kit comprising a collagen composition and a buffer solution is provided. In another embodiment, a kit comprising lyophilized collagen, a hydrochloric acid solution, and a buffer solution is provided.

Several additional embodiments are described by the following enumerated clauses. Any applicable combination of these embodiments is also contemplated.

1. A method for preparing a matrix, said method comprising polymerizing collagen using a single mixing step comprising mixing a collagen composition with a buffer solution to form a collagen solution, and polymerizing the collagen in the collagen solution to form the matrix.

2. The method of clause 1 comprising incubating the collagen solution at greater than about 25° C. to promote polymerization of the collagen in the collagen solution.

3. The method of clause 1 or 2 comprising incubating the collagen solution at about 37° C. to promote polymerization of the collagen in the collagen solution.

4. The method of any one of clauses 1 to 3 wherein the collagen comprises collagen oligomers.

5. The method of any one of clauses 1 to 4 wherein the collagen consists of collagen oligomers.

6. The method of clause 4 wherein the collagen further comprises telocollagen.

7. The method of clause 4 wherein the collagen further comprises atelocollagen.

8. The method of clause 4 wherein the collagen comprising collagen oligomers is obtained from a tissue containing collagen oligomers, from cells producing collagen oligomers, or by chemically crosslinking collagen to obtain the collagen oligomers.

9. The method of any one of clauses 1 to 8 wherein the collagen is derived from porcine skin tissue.

10. The method of any one of clauses 1 to 9 wherein the collagen composition further comprises an acid.

11. The method of clause 10 wherein the acid is selected from the group consisting of hydrochloric acid, acetic acid, lactic acid, formic acid, citric acid, sulfuric acid, and phosphoric acid.

12. The method of clause 11 wherein the acid is hydrochloric acid.

13. The method of clause 12 wherein the hydrochloric acid is about 0.005 N to about 0.1 N hydrochloric acid.

14. The method of clause 12 or 13 wherein the hydrochloric acid is about 0.01 N hydrochloric acid.

15. The method of any one of clauses 1 to 14 wherein the collagen is at a concentration of about 0.1 mg/ml to about 40 mg/ml in the collagen solution.

16. The method of any one of clauses 1 to 15 wherein the collagen is at a concentration of about 0.1 mg/ml to about 5 mg/ml in the collagen solution.

17. The method of any one of clauses 1 to 16 wherein the collagen is at a concentration of about 0.5 mg/ml to about 4 mg/ml in the collagen solution.

18. The method of any one of clauses 1 to 13 wherein the collagen composition is sterilized.

19. The method of any one of clauses 1 to 18 wherein the collagen composition, the collagen solution, or the collagen matrix is sterilized by a method selected from the group consisting of exposure to chloroform, viral filtration, sterile filtration, ultraviolet radiation, gamma irradiation, E-beam, and combinations thereof.

20. The method of any one of clauses 1 to 19 wherein the collagen composition is sterilized by filtration.

21. The method of any one of clauses 1 to 20 wherein the buffer solution comprises about 0.03 mM to about 0.2 mM $MgCl_2$.

22. The method of any one of clauses 1 to 20 wherein the buffer solution comprises about 0.002 mM to about 0.02 mM $MgCl_2$.

23. The method of any one of clauses 1 to 20 wherein the buffer solution comprises less than about 0.02 mM $MgCl_2$.

24. The method of any one of clauses 1 to 20 wherein the buffer solution does not comprise $MgCl_2$.

25. The method of any one of clauses 1 to 24 wherein the buffer solution further comprises about 0.3 mM to about 3 mM $KH_2PO_4$.

26. The method of any one of clauses 1 to 25 wherein the buffer solution further comprises about 1 mM to about 10 M $Na_2HPO_4$.

27. The method of any one of clauses 1 to 26 wherein the buffer solution further comprises about 0.1 mM to about 4 mM KCl.

28. The method of any one of clauses 1 to 27 wherein the buffer solution further comprises about 0.02 M to about 0.3 M NaCl.

29. The method of any one of clauses 1 to 28 wherein the buffer solution further comprises about 0.002 N to about 0.02 N NaOH.

30. The method of any one of clauses 1 to 29 wherein the buffer solution further comprises about 0.5 weight percent to about 5 weight percent of glucose.

31. The method of any one of clauses 1 to 29 wherein the buffer solution comprises about 0.5 weight percent glucose or less.

32. The method of any one of clauses 1 to 31 further comprising adding cells to the collagen solution.

33. The method of any one of clauses 1 to 32 wherein the matrix comprises collagen fibrils.

34. A collagen matrix prepared according to the method of any one of clauses 1 to 33.

35. The collagen matrix of clause 34 wherein the collagen matrix is a medical graft.

36. The collagen matrix of clause 35 wherein the medical graft has a use selected from the group consisting of a tissue graft material, an injectable graft material, a wound dressing, a hemostatic dressing, a delivery vehicle for therapeutic cells, and a delivery vehicle for a therapeutic agent.

37. The collagen matrix of clause 35 wherein the collagen matrix is used for research purposes.

38. The collagen matrix of clause 37 wherein the collagen matrix is used for drug toxicity testing or drug development.

39. A kit comprising a collagen composition and a buffer solution.

40. The kit of clause 39 wherein the buffer solution comprises about 0.03 mM to about 0.2 mM $MgCl_2$.

41. The kit of clause 39 wherein the buffer solution comprises about 0.002 mM to about 0.02 mM $MgCl_2$.

42. The kit of clause 39 wherein the buffer solution comprises less than about 0.02 mM $MgCl_2$.

43. The kit of clause 39 wherein the buffer solution does not comprise $MgCl_2$.

44. The kit of any one of clauses 39 to 43 wherein the buffer solution further comprises about 0.003 M to about 0.03 M $KH_2PO_4$.

45. The kit of any one of clauses 39 to 44 wherein the buffer solution further comprises about 0.01 M to about 0.1 M $Na_2HPO_4$.

46. The kit of any one of clauses 39 to 45 wherein the buffer solution further comprises about 0.001 M to about 0.04 M KCl.

47. The kit of any one of clauses 39 to 46 wherein the buffer solution further comprises about 0.2 M to about 3.0 M NaCl.

48. The kit of any one of clauses 39 to 47 wherein the buffer solution further comprises about 0.02 N to about 0.2 N NaOH.

49. The kit of any one of clauses 39 to 48 wherein the buffer solution further comprises about 0.2 weight percent to about 5 weight percent of glucose.

50. The kit of any one of clauses 39 to 48 wherein the buffer solution comprises about 0.5 weight percent glucose or less.

51. The kit of any one of clauses 39 to 50 wherein the collagen in the collagen solution is at a concentration of about 0.1 mg/ml to about 40 mg/ml.

52. The kit of any one of clauses 39 to 51 wherein the collagen in the collagen solution is at a concentration of about 0.1 mg/ml to about 5 mg/ml.

53. The kit of any one of clauses 39 to 52 wherein the collagen solution comprises about 0.005 N hydrochloric acid to about 0.1 N hydrochloric acid.

54. The kit of any one of clauses 39 to 53 wherein the buffer solution is capable of polymerizing the collagen using a single mixing step comprising mixing the collagen composition with the buffer solution.

55. The kit of any one of clauses 39 to 54 wherein the collagen composition and the buffer solution are in separate containers.

56. The kit of clause 55 wherein the containers are sterilized vials.

57. The kit of clause 55 wherein the containers comprise separate compartments of a dual syringe.

58. The kit of clause 57 wherein the dual syringe comprises a mixing element.

59. The kit of clause 57 wherein the dual syringe is sterilized.

60. The kit of any one of clauses 39 to 59 further comprising instructions for use of components of the kit.

61. A method for preparing a matrix, said method comprising polymerizing collagen by mixing a collagen composition with a buffer solution to form a collagen solution, and polymerizing the collagen in the collagen solution to form the matrix wherein the buffer solution does not contain magnesium ions or manganese ions.

62. The method of clause 61 comprising incubating the collagen solution at greater than about 25° C. to promote polymerization of the collagen in the collagen solution.

63. The method of clause 61 or 62 comprising incubating the collagen solution at about 37° C. to promote polymerization of the collagen in the collagen solution.

64. The method of any one of clauses 61 to 63 wherein the collagen comprises collagen oligomers.

65. The method of any one of clauses 61 to 63 wherein the collagen consists of collagen oligomers.

66. The method of clause 64 wherein the collagen further comprises telocollagen.

67. The method of clause 64 wherein the collagen further comprises atelocollagen.

68. The method of clause 64 wherein the collagen comprising collagen oligomers is obtained from a tissue containing collagen oligomers, from cells producing collagen oligomers, or by chemically crosslinking the collagen to obtain the collagen oligomers.

69. The method of any one of clauses 61 to 68 wherein the collagen is derived from porcine skin tissue.

70. The method of any one of clauses 61 to 69 wherein the collagen composition further comprises an acid.

71. The method of clause 70 wherein the acid is selected from the group consisting of hydrochloric acid, acetic acid, lactic acid, formic acid, citric acid, sulfuric acid, and phosphoric acid.

72. The method of clause 71 wherein the acid is hydrochloric acid.

73. The method of clause 72 wherein the hydrochloric acid is about 0.005 N to about 0.1 N hydrochloric acid.

74. The method of clause 72 or 73 wherein the hydrochloric acid is about 0.01 N hydrochloric acid.

75. The method of any one of clauses 61 to 74 wherein the collagen is at a concentration of about 0.1 mg/ml to about 40 mg/ml in the collagen solution.

76. The method of any one of clauses 61 to 75 wherein the collagen is at a concentration of about 0.1 mg/ml to about 5 mg/ml in the collagen solution.

77. The method of any one of clauses 61 to 76 wherein the collagen is at a concentration of about 0.5 mg/ml to about 4 mg/ml in the collagen solution.

78. The method of any one of clauses 61 to 77 wherein the collagen composition is sterilized.

79. The method of any one of clauses 61 to 78 wherein the collagen composition, the collagen solution, or the collagen matrix is sterilized by a method selected from the group consisting of exposure to chloroform, viral filtration, sterile filtration, ultraviolet radiation, gamma irradiation, E-beam, and combinations thereof.

80. The method of any one of clauses 61 to 79 wherein the collagen composition is sterilized by filtration.

81. The method of any one of clauses 61 to 80 wherein the buffer solution further comprises about 0.3 mM to about 3 mM $KH_2PO_4$.

82. The method of any one of clauses 61 to 81 wherein the buffer solution further comprises about 1 mM to about 10 M $Na_2HPO_4$.

83. The method of any one of clauses 61 to 82 wherein the buffer solution further comprises about 0.1 mM to about 4 mM KCl.

84. The method of any one of clauses 61 to 83 wherein the buffer solution further comprises about 0.02 M to about 0.3 M NaCl.

85. The method of any one of clauses 61 to 84 wherein the buffer solution further comprises about 0.002 N to about 0.02 N NaOH.

86. The method of any one of clauses 61 to 85 wherein the buffer solution further comprises about 0.5 weight percent to about 5 weight percent of glucose.

87. The method of any one of clauses 61 to 85 wherein the buffer solution comprises about 0.5 weight percent of glucose or less.

88. The method of any one of clauses 61 to 87 further comprising adding cells to the collagen solution.

89. The method of any one of clauses 61 to 88 wherein the matrix comprises collagen fibrils.

90. A collagen matrix prepared according to the method of any one of clauses 61 to 89.

91. The collagen matrix of clause 90 wherein the collagen matrix is a medical graft.

92. The collagen matrix of clause 91 wherein the medical graft has a use selected from the group consisting of a tissue graft material, an injectable graft material, a wound dressing, a hemostatic dressing, a delivery vehicle for therapeutic cells, and a delivery vehicle for a therapeutic agent.

93. The collagen matrix of clause 90 wherein the collagen matrix is used for research purposes.

94. The collagen matrix of clause 93 wherein the collagen matrix is used for drug toxicity testing or drug development.

95. A kit comprising lyophilized collagen, a hydrochloric acid solution, and a buffer solution.

96. The kit of clause 95 wherein the buffer solution comprises about 0.03 mM to about 0.2 mM $MgCl_2$.

97. The kit of clause 95 wherein the buffer solution comprises about 0.002 mM to about 0.02 mM $MgCl_2$.

98. The kit of clause 95 wherein the buffer solution comprises less than about 0.02 mM $MgCl_2$.

99. The kit of clause 95 wherein the buffer solution does not comprise $MgCl_2$.

100. The kit of any one of clauses 95 to 99 wherein the buffer solution further comprises about 0.003 M to about 0.03 M $KH_2PO_4$.

101. The kit of any one of clauses 95 to 100 wherein the buffer solution further comprises about 0.01 M to about 0.1 M $Na_2HPO_4$.

102. The kit of any one of clauses 95 to 101 wherein the buffer solution further comprises about 0.001 M to about 0.04 M KCl.

103. The kit of any one of clauses 95 to 102 wherein the buffer solution further comprises about 0.2 M to about 3.0 M NaCl.

104. The kit of any one of clauses 95 to 103 wherein the buffer solution further comprises about 0.02 N to about 0.2 N NaOH.

105. The kit of any one of clauses 95 to 104 wherein the buffer solution further comprises about 0.2 weight percent to about 5 weight percent of glucose.

106. The kit of any one of clauses 95 to 105 wherein the buffer solution comprises about 0.5 weight percent glucose or less.

107. The kit of any one of clauses 95 to 106 wherein the hydrochloric acid solution comprises about 0.005 N hydrochloric acid to about 0.1 N hydrochloric acid.

108. The kit of any one of clauses 95 to 107 wherein the buffer solution is capable of polymerizing collagen using a single mixing step comprising mixing the buffer solution with the lyophilized collagen reconstituted in the hydrochloric acid solution.

109. The kit of any one of clauses 95 to 108 wherein the lyophilized collagen, the hydrochloric acid solution, and the buffer solution are in separate containers.

110. The kit of any one of clauses 95 to 109 further comprising instructions for use of components of the kit.

111. A method for preparing a matrix, said method comprising polymerizing collagen using a single mixing step comprising mixing a collagen composition with a buffer solution to form a collagen solution, wherein the collagen in the collagen solution polymerizes to form the matrix.

112. The method of any one of clauses 1 to 33, 61 to 89, or 111 wherein the collagen is soluble collagen.

113. The method of any one of clauses 1 to 19, 21 to 33, 61 to 79, 81 to 89, or 111 to 112 wherein the collagen composition, the collagen solution, and/or the collagen matrix is sterilized using ultraviolet radiation.

114. The method of clause 113 wherein the collagen matrix that results from collagen polymerization maintains a polymerization property relative to a collagen composition this is not irradiated, a collagen solution that is not irradiated, or a collagen matrix that is not irradiated, respectively.

115. The method of clause 114 wherein the polymerization property is shear storage modulus.

116. The method of any one of clauses 113 to 115 wherein the radiation dose ranges from about 5 mJ/cm2 to about 800 mJ/cm2.

117. The method of any one of clauses 113 to 115 wherein the radiation dose ranges from about 30 mJ/cm2 to about 300 mJ/cm2.

118. The method of any one of clauses 113 to 117 wherein the sterilization inactivates viruses.

119. The collagen matrix of any one of clauses 34 to 38 or 90 to 94 wherein the collagen matrix is sterilized using ultraviolet radiation.

120. The collagen matrix of clause 119 wherein the collagen matrix maintains a polymerization property relative to a collagen matrix that is not irradiated.

121. The collagen matrix of clause 120 wherein the polymerization property is shear storage modulus.

122. The collagen matrix of any one of clauses 119 to 121 wherein the radiation dose ranges from about 5 mJ/cm2 to about 800 mJ/cm2.

123. The collagen matrix of any one of clauses 119 to 121 wherein the radiation dose ranges from about 30 mJ/cm2 to about 300 mJ/cm2.

124. The collagen matrix of any one of clauses 119 to 123 wherein the sterilization inactivates viruses.

125. The kit of any one of clauses 39 to 60 or 95 to 110 wherein the collagen composition or the lyophilized collagen is sterilized using ultraviolet radiation.

126. The kit of clause 125 wherein the collagen matrix that results from collagen polymerization maintains a polymerization property relative to a collagen composition this is not irradiated or to lyophilized collagen that is not irradiated, respectively.

127. The kit of clause 126 wherein the polymerization property is shear storage modulus.

128. The kit of any one of clauses 125 to 127 wherein the radiation dose ranges from about 5 mJ/cm2 to about 800 mJ/cm2.

129. The kit of any one of clauses 125 to 127 wherein the radiation dose ranges from about 30 mJ/cm2 to about 300 mJ/cm2.

130. The kit of any one of clauses 125 to 129 wherein the sterilization inactivates viruses.

131. The method of any one of clauses 1 to 19, 21 to 33, 61 to 79, 81 to 89, or 111 to 118 wherein the collagen composition, the collagen solution, and/or the collagen matrix is sterilized using UVC irradiation.

132. The method of any one of clauses 1 to 19, 21 to 33, 61 to 79, 81 to 89, or 111 to 118 wherein the collagen composition, the collagen solution, and/or the collagen matrix is sterilized using UVC irradiation and sterile filtration.

133. The collagen matrix of any one of clauses 34 to 38, 90 to 94, or 119 to 124 wherein the collagen matrix is sterilized using UVC irradiation.

134. The collagen matrix of any one of clauses 34 to 38, 90 to 94, or 119 to 124 wherein the collagen matrix is sterilized using UVC irradiation and sterile filtration.

135. The kit of any one of clauses 39 to 60, 95 to 110, or 125 to 130 wherein the collagen composition or the lyophilized collagen is sterilized using UVC irradiation.

136. The kit of any one of clauses 39 to 60, 95 to 110, or 125 to 130 wherein the collagen composition or the lyophilized collagen is sterilized using UVC irradiation and sterile filtration.

DETAILED DESCRIPTION OF THE ILLUSTRATIVE EMBODIMENTS

Figure 1:
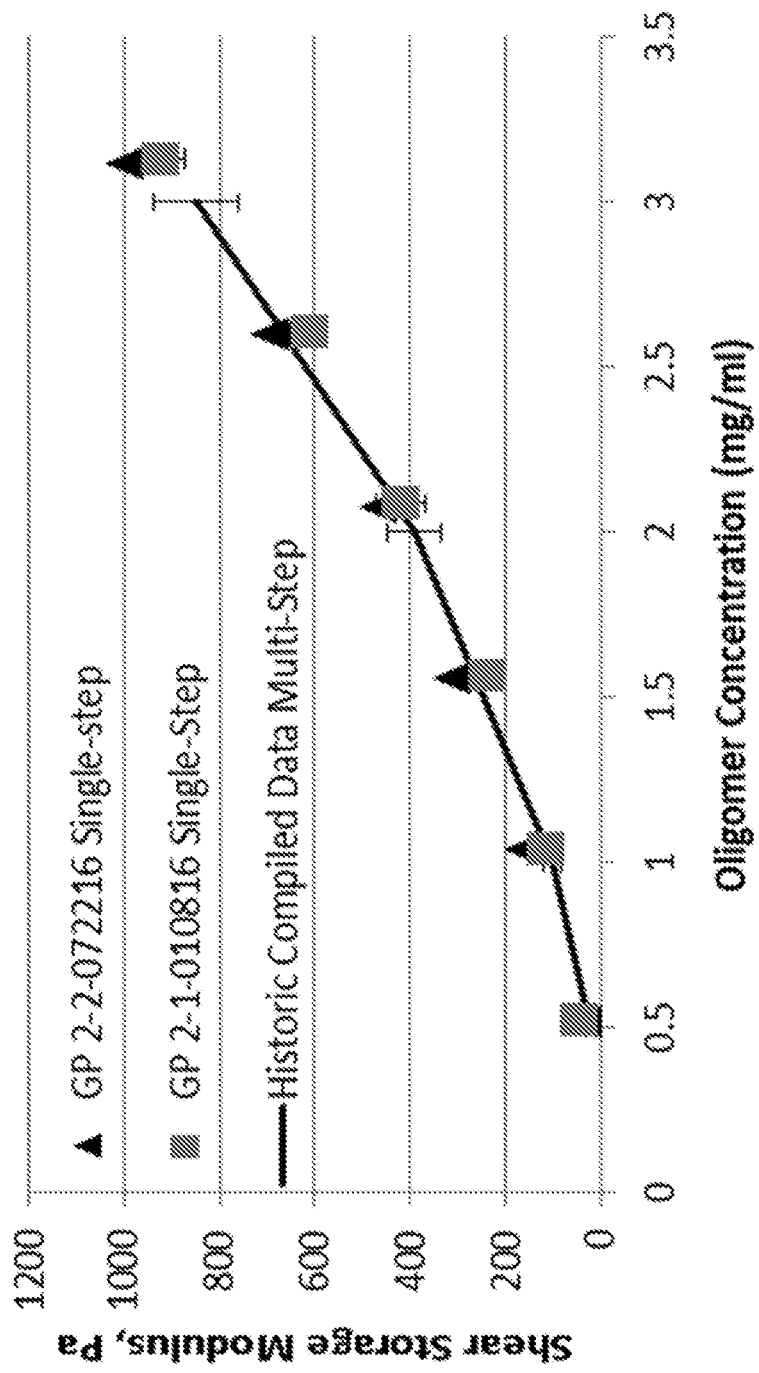
FIG. 1 shows shear storage modulus for collagen-based matrices polymerized at different oligomer concentrations. The polymerization capacity for a single-step assembly is similar to that obtained with a conventional multi-step procedure.

As used herein, "sterilized" means removing contaminants including, but not limited to, infectious agents. For example, contaminants (e.g., viruses) can be removed by inactivation, reduction in number or amount, or by inhibition of activity of contaminating agents, whether infectious or not.

As used herein, "purified" means removing contaminants including, but not limited to, cellular contaminants, nucleotide contaminants, and endotoxins. means inactivating all viruses, whether infectious or not, reducing the number of infectious viruses, or inhibiting the activity of viruses, whether infectious or not.

As used herein "oligomer" or "oligomers" in relation to collagen means collagen monomers (otherwise known as telocollagen) covalently attached to each other (e.g., collagen monomers attached to each other to form dimers, trimers, etc.).

In one embodiment, a method for preparing a matrix is provided. The method comprises polymerizing collagen using a single mixing step comprising mixing a collagen composition with a buffer solution to form a collagen solution, and polymerizing the collagen in the collagen solution to form the matrix.

In another embodiment, a method for preparing a matrix is provided. The method comprises polymerizing collagen by mixing a collagen composition with a buffer solution to form a collagen solution, and polymerizing the collagen in the collagen solution to form the matrix wherein the buffer solution does not contain magnesium ions or manganese ions.

In yet another embodiment, a method for preparing a matrix is provided. The method comprises polymerizing collagen using a single mixing step comprising mixing a collagen composition with a buffer solution to form a collagen solution, wherein the collagen in the collagen solution polymerizes to form the matrix.

In still other embodiments, a collagen matrix prepared according to any of the preceding methods is provided. In yet another embodiment, a kit comprising a collagen composition and a buffer solution is provided. In another embodiment, a kit comprising lyophilized collagen, a hydrochloric acid solution, and a buffer solution is provided.

Several additional embodiments are described by the following enumerated clauses. Any applicable combination of these embodiments is also contemplated, and any applicable combination of these embodiments with the embodiments described in this DETAILED DESCRIPTION OF THE ILLUSTRATIVE EMBODIMENTS section of the application is also contemplated.

1. A method for preparing a matrix, said method comprising polymerizing collagen using a single mixing step comprising mixing a collagen composition with a buffer solution to form a collagen solution, and polymerizing the collagen in the collagen solution to form the matrix.

2. The method of clause 1 comprising incubating the collagen solution at greater than about 25° C. to promote polymerization of the collagen in the collagen solution.

3. The method of clause 1 or 2 comprising incubating the collagen solution at about 37° C. to promote polymerization of the collagen in the collagen solution.

4. The method of any one of clauses 1 to 3 wherein the collagen comprises collagen oligomers.

5. The method of any one of clauses 1 to 4 wherein the collagen consists of collagen oligomers.

6. The method of clause 4 wherein the collagen further comprises telocollagen.

7. The method of clause 4 wherein the collagen further comprises atelocollagen.

8. The method of clause 4 wherein the collagen comprising collagen oligomers is obtained from a tissue containing collagen oligomers, from cells producing collagen oligomers, or by chemically crosslinking collagen to obtain the collagen oligomers.

9. The method of any one of clauses 1 to 8 wherein the collagen is derived from porcine skin tissue.

10. The method of any one of clauses 1 to 9 wherein the collagen composition further comprises an acid.

11. The method of clause 10 wherein the acid is selected from the group consisting of hydrochloric acid, acetic acid, lactic acid, formic acid, citric acid, sulfuric acid, and phosphoric acid.

12. The method of clause 11 wherein the acid is hydrochloric acid.

13. The method of clause 12 wherein the hydrochloric acid is about 0.005 N to about 0.1 N hydrochloric acid.

14. The method of clause 12 or 13 wherein the hydrochloric acid is about 0.01 N hydrochloric acid.

15. The method of any one of clauses 1 to 14 wherein the collagen is at a concentration of about 0.1 mg/ml to about 40 mg/ml in the collagen solution.

16. The method of any one of clauses 1 to 15 wherein the collagen is at a concentration of about 0.1 mg/ml to about 5 mg/ml in the collagen solution.

17. The method of any one of clauses 1 to 16 wherein the collagen is at a concentration of about 0.5 mg/ml to about 4 mg/ml in the collagen solution.

18. The method of any one of clauses 1 to 13 wherein the collagen composition is sterilized.

19. The method of any one of clauses 1 to 18 wherein the collagen composition, the collagen solution, or the collagen matrix is sterilized by a method selected from the group consisting of exposure to chloroform, viral filtration, sterile filtration, gamma irradiation, ultraviolet radiation, E-beam, and combinations thereof.

20. The method of any one of clauses 1 to 19 wherein the collagen composition is sterilized by filtration.

21. The method of any one of clauses 1 to 20 wherein the buffer solution comprises about 0.03 mM to about 0.2 mM $MgCl_2$.

22. The method of any one of clauses 1 to 20 wherein the buffer solution comprises about 0.002 mM to about 0.02 mM $MgCl_2$.

23. The method of any one of clauses 1 to 20 wherein the buffer solution comprises less than about 0.02 mM $MgCl_2$.

24. The method of any one of clauses 1 to 20 wherein the buffer solution does not comprise $MgCl_2$.

25. The method of any one of clauses 1 to 24 wherein the buffer solution further comprises about 0.3 mM to about 3 mM $KH_2PO_4$.

26. The method of any one of clauses 1 to 25 wherein the buffer solution further comprises about 1 mM to about 10 M $Na_2HPO_4$.

27. The method of any one of clauses 1 to 26 wherein the buffer solution further comprises about 0.1 mM to about 4 mM KCl.

28. The method of any one of clauses 1 to 27 wherein the buffer solution further comprises about 0.02 M to about 0.3 M NaCl.

29. The method of any one of clauses 1 to 28 wherein the buffer solution further comprises about 0.002 N to about 0.02 N NaOH.

30. The method of any one of clauses 1 to 29 wherein the buffer solution further comprises about 0.5 weight percent to about 5 weight percent of glucose.

31. The method of any one of clauses 1 to 29 wherein the buffer solution comprises about 0.5 weight percent glucose or less.

32. The method of any one of clauses 1 to 31 further comprising adding cells to the collagen solution.

33. The method of any one of clauses 1 to 32 wherein the matrix comprises collagen fibrils.

34. A collagen matrix prepared according to the method of any one of clauses 1 to 33.

35. The collagen matrix of clause 34 wherein the collagen matrix is a medical graft.

36. The collagen matrix of clause 35 wherein the medical graft has a use selected from the group consisting of a tissue graft material, an injectable graft material, a wound dressing, a hemostatic dressing, a delivery vehicle for therapeutic cells, and a delivery vehicle for a therapeutic agent.

37. The collagen matrix of clause 35 wherein the collagen matrix is used for research purposes.

38. The collagen matrix of clause 37 wherein the collagen matrix is used for drug toxicity testing or drug development.

39. A kit comprising a collagen composition and a buffer solution.

40. The kit of clause 39 wherein the buffer solution comprises about 0.03 mM to about 0.2 mM $MgCl_2$.

41. The kit of clause 39 wherein the buffer solution comprises about 0.002 mM to about 0.02 mM $MgCl_2$.

42. The kit of clause 39 wherein the buffer solution comprises less than about 0.02 mM $MgCl_2$.

43. The kit of clause 39 wherein the buffer solution does not comprise $MgCl_2$.

44. The kit of any one of clauses 39 to 43 wherein the buffer solution further comprises about 0.003M to about 0.03 M $KH_2PO_4$.

45. The kit of any one of clauses 39 to 44 wherein the buffer solution further comprises about 0.01 M to about 0.1 M $Na_2HPO_4$.

46. The kit of any one of clauses 39 to 45 wherein the buffer solution further comprises about 0.001 M to about 0.04 M KCl.

47. The kit of any one of clauses 39 to 46 wherein the buffer solution further comprises about 0.2 M to about 3.0 M NaCl.

48. The kit of any one of clauses 39 to 47 wherein the buffer solution further comprises about 0.02 N to about 0.2 N NaOH.

49. The kit of any one of clauses 39 to 48 wherein the buffer solution further comprises about 0.2 weight percent to about 5 weight percent of glucose.

50. The kit of any one of clauses 39 to 48 wherein the buffer solution comprises about 0.5 weight percent glucose or less.

51. The kit of any one of clauses 39 to 50 wherein the collagen in the collagen solution is at a concentration of about 0.1 mg/ml to about 40 mg/ml.

52. The kit of any one of clauses 39 to 51 wherein the collagen in the collagen solution is at a concentration of about 0.1 mg/ml to about 5 mg/ml.

53. The kit of any one of clauses 39 to 52 wherein the collagen solution comprises about 0.005 N hydrochloric acid to about 0.1 N hydrochloric acid.

54. The kit of any one of clauses 39 to 53 wherein the buffer solution is capable of polymerizing the collagen using a single mixing step comprising mixing the collagen composition with the buffer solution.

55. The kit of any one of clauses 39 to 54 wherein the collagen composition and the buffer solution are in separate containers.

56. The kit of clause 55 wherein the containers are sterilized vials.

57. The kit of clause 55 wherein the containers comprise separate compartments of a dual syringe.

58. The kit of clause 57 wherein the dual syringe comprises a mixing element.

59. The kit of clause 57 wherein the dual syringe is sterilized.

60. The kit of any one of clauses 39 to 59 further comprising instructions for use of components of the kit.

61. A method for preparing a matrix, said method comprising polymerizing collagen by mixing a collagen composition with a buffer solution to form a collagen solution, and polymerizing the collagen in the collagen solution to form the matrix wherein the buffer solution does not contain magnesium ions or manganese ions.

62. The method of clause 61 comprising incubating the collagen solution at greater than about 25° C. to promote polymerization of the collagen in the collagen solution.

63. The method of clause 61 or 62 comprising incubating the collagen solution at about 37° C. to promote polymerization of the collagen in the collagen solution.

64. The method of any one of clauses 61 to 63 wherein the collagen comprises collagen oligomers.

65. The method of any one of clauses 61 to 63 wherein the collagen consists of collagen oligomers.

66. The method of clause 64 wherein the collagen further comprises telocollagen.

67. The method of clause 64 wherein the collagen further comprises atelocollagen.

68. The method of clause 64 wherein the collagen comprising collagen oligomers is obtained from a tissue containing collagen oligomers, from cells producing collagen oligomers, or by chemically crosslinking the collagen to obtain the collagen oligomers.

69. The method of any one of clauses 61 to 68 wherein the collagen is derived from porcine skin tissue.

70. The method of any one of clauses 61 to 69 wherein the collagen composition further comprises an acid.

71. The method of clause 70 wherein the acid is selected from the group consisting of hydrochloric acid, acetic acid, lactic acid, formic acid, citric acid, sulfuric acid, and phosphoric acid.

72. The method of clause 71 wherein the acid is hydrochloric acid.

73. The method of clause 72 wherein the hydrochloric acid is about 0.005 N to about 0.1 N hydrochloric acid.

74. The method of clause 72 or 73 wherein the hydrochloric acid is about 0.01 N hydrochloric acid.

75. The method of any one of clauses 61 to 74 wherein the collagen is at a concentration of about 0.1 mg/ml to about 40 mg/ml in the collagen solution.

76. The method of any one of clauses 61 to 75 wherein the collagen is at a concentration of about 0.1 mg/ml to about 5 mg/ml in the collagen solution.

77. The method of any one of clauses 61 to 76 wherein the collagen is at a concentration of about 0.5 mg/ml to about 4 mg/ml in the collagen solution.

78. The method of any one of clauses 61 to 77 wherein the collagen composition is sterilized.

79. The method of any one of clauses 61 to 78 wherein the collagen composition, the collagen solution, or the collagen matrix is sterilized by a method selected from the group consisting of exposure to chloroform, viral filtration, sterile filtration, gamma irradiation, ultraviolet radiation, E-beam, and combinations thereof.

80. The method of any one of clauses 61 to 79 wherein the collagen composition is sterilized by filtration.

81. The method of any one of clauses 61 to 80 wherein the buffer solution further comprises about 0.3 mM to about 3 mM $KH_2PO_4$.

82. The method of any one of clauses 61 to 81 wherein the buffer solution further comprises about 1 mM to about 10 M $Na_2HPO_4$.

83. The method of any one of clauses 61 to 82 wherein the buffer solution further comprises about 0.1 mM to about 4 mM KCl.

84. The method of any one of clauses 61 to 83 wherein the buffer solution further comprises about 0.02 M to about 0.3 M NaCl.

85. The method of any one of clauses 61 to 84 wherein the buffer solution further comprises about 0.002 N to about 0.02 N NaOH.

86. The method of any one of clauses 61 to 85 wherein the buffer solution further comprises about 0.5 weight percent to about 5 weight percent of glucose.

87. The method of any one of clauses 61 to 85 wherein the buffer solution comprises about 0.5 weight percent of glucose or less.

88. The method of any one of clauses 61 to 87 further comprising adding cells to the collagen solution.

89. The method of any one of clauses 61 to 88 wherein the matrix comprises collagen fibrils.

90. A collagen matrix prepared according to the method of any one of clauses 61 to 89.

91. The collagen matrix of clause 90 wherein the collagen matrix is a medical graft.

92. The collagen matrix of clause 91 wherein the medical graft has a use selected from the group consisting of a tissue graft material, an injectable graft material, a wound dressing, a hemostatic dressing, a delivery vehicle for therapeutic cells, and a delivery vehicle for a therapeutic agent.

93. The collagen matrix of clause 90 wherein the collagen matrix is used for research purposes.

94. The collagen matrix of clause 93 wherein the collagen matrix is used for drug toxicity testing or drug development.

95. A kit comprising lyophilized collagen, a hydrochloric acid solution, and a buffer solution.

96. The kit of clause 95 wherein the buffer solution comprises about 0.03 mM to about 0.2 mM $MgCl_2$.

97. The kit of clause 95 wherein the buffer solution comprises about 0.002 mM to about 0.02 mM $MgCl_2$. 98. The kit of clause 95 wherein the buffer solution comprises less than about 0.02 mM $MgCl_2$.

99. The kit of clause 95 wherein the buffer solution does not comprise $MgCl_2$.

100. The kit of any one of clauses 95 to 99 wherein the buffer solution further comprises about 0.003 M to about 0.03 M $KH_2PO_4$.

101. The kit of any one of clauses 95 to 100 wherein the buffer solution further comprises about 0.01 M to about 0.1 M $Na_2HPO_4$.

102. The kit of any one of clauses 95 to 101 wherein the buffer solution further comprises about 0.001 M to about 0.04 M KCl.

103. The kit of any one of clauses 95 to 102 wherein the buffer solution further comprises about 0.2 M to about 3.0 M NaCl.

104. The kit of any one of clauses 95 to 103 wherein the buffer solution further comprises about 0.02 N to about 0.2 N NaOH.

105. The kit of any one of clauses 95 to 104 wherein the buffer solution further comprises about 0.2 weight percent to about 5 weight percent of glucose.

106. The kit of any one of clauses 95 to 105 wherein the buffer solution comprises about 0.5 weight percent glucose or less.

107. The kit of any one of clauses 95 to 106 wherein the hydrochloric acid solution comprises about 0.005 N hydrochloric acid to about 0.1 N hydrochloric acid.

108. The kit of any one of clauses 95 to 107 wherein the buffer solution is capable of polymerizing collagen using a single mixing step comprising mixing the buffer solution with the lyophilized collagen reconstituted in the hydrochloric acid solution.

109. The kit of any one of clauses 95 to 108 wherein the lyophilized collagen, the hydrochloric acid solution, and the buffer solution are in separate containers.

110. The kit of any one of clauses 95 to 109 further comprising instructions for use of components of the kit.

111. A method for preparing a matrix, said method comprising polymerizing collagen using a single mixing step comprising mixing a collagen composition with a buffer solution to form a collagen solution, wherein the collagen in the collagen solution polymerizes to form the matrix.

112. The method of any one of clauses 1 to 33, 61 to 89, or 111 wherein the collagen is soluble collagen.

113. The method of any one of clauses 1 to 19, 21 to 33, 61 to 79, 81 to 89, or 111 to 112 wherein the collagen composition, the collagen solution, and/or the collagen matrix is sterilized using ultraviolet radiation.

114. The method of clause 113 wherein the collagen matrix that results from collagen polymerization maintains a polymerization property relative to a collagen composition this is not irradiated, a collagen solution that is not irradiated, or a collagen matrix that is not irradiated, respectively.

115. The method of clause 114 wherein the polymerization property is shear storage modulus.

116. The method of any one of clauses 113 to 115 wherein the radiation dose ranges from about 5 $mJ/cm^2$ to about 800 $mJ/cm^2$.

117. The method of any one of clauses 113 to 115 wherein the radiation dose ranges from about 30 $mJ/cm^2$ to about 300 $mJ/cm^2$.

118. The method of any one of clauses 113 to 117 wherein the sterilization inactivates viruses.

119. The collagen matrix of any one of clauses 34 to 38 or 90 to 94 wherein the collagen matrix is sterilized using ultraviolet radiation.

120. The collagen matrix of clause 119 wherein the collagen matrix maintains a polymerization property relative to a collagen matrix that is not irradiated.

121. The collagen matrix of clause 120 wherein the polymerization property is shear storage modulus.

122. The collagen matrix of any one of clauses 119 to 121 wherein the radiation dose ranges from about 5 $mJ/cm^2$ to about 800 $mJ/cm^2$.

123. The collagen matrix of any one of clauses 119 to 121 wherein the radiation dose ranges from about 30 mJ/cm$^2$ to about 300 mJ/cm$^2$.

124. The collagen matrix of any one of clauses 119 to 123 wherein the sterilization inactivates viruses.

125. The kit of any one of clauses 39 to 60 or 95 to 110 wherein the collagen composition or the lyophilized collagen is sterilized using ultraviolet radiation.

126. The kit of clause 125 wherein the collagen matrix that results from collagen polymerization maintains a polymerization property relative to a collagen composition this is not irradiated or to lyophilized collagen that is not irradiated, respectively.

127. The kit of clause 126 wherein the polymerization property is shear storage modulus.

128. The kit of any one of clauses 125 to 127 wherein the radiation dose ranges from about 5 mJ/cm$^2$ to about 800 mJ/cm$^2$.

129. The kit of any one of clauses 125 to 127 wherein the radiation dose ranges from about 30 mJ/cm$^2$ to about 300 mJ/cm$^2$.

130. The kit of any one of clauses 125 to 129 wherein the sterilization inactivates viruses.

131. The method of any one of clauses 1 to 19, 21 to 33, 61 to 79, 81 to 89, or 111 to 118 wherein the collagen composition, the collagen solution, and/or the collagen matrix is sterilized using UVC irradiation.

132. The method of any one of clauses 1 to 19, 21 to 33, 61 to 79, 81 to 89, or 111 to 118 wherein the collagen composition, the collagen solution, and/or the collagen matrix is sterilized using UVC irradiation and sterile filtration.

133. The collagen matrix of any one of clauses 34 to 38, 90 to 94, or 119 to 124 wherein the collagen matrix is sterilized using UVC irradiation.

134. The collagen matrix of any one of clauses 34 to 38, 90 to 94, or 119 to 124 wherein the collagen matrix is sterilized using UVC irradiation and sterile filtration.

135. The kit of any one of clauses 39 to 60, 95 to 110, or 125 to 130 wherein the collagen composition or the lyophilized collagen is sterilized using UVC irradiation.

136. The kit of any one of clauses 39 to 60, 95 to 110, or 125 to 130 wherein the collagen composition or the lyophilized collagen is sterilized using UVC irradiation and sterile filtration.

As would be understood by a skilled artisan, polymerization, self-assembly, self-assembled, fibril formation, and matrix-forming capability have the same meaning, and as would be understood by a skilled artisan the matrix can be in fibrillar form. For preparation of the collagen for use in the methods and compositions described herein, any method known in the art for preparing collagen can be used. In illustrative embodiments, the collagen can be prepared by methods described in Bailey J L, Critser P J, Whittington C, Kuske J L, Yoder M C, Voytik-Harbin S L; Collagen oligomers modulate physical and biological properties of three-dimensional self-assembled matrices, *Biopolymers* (2011) 95(2):77-93, Kreger S T, Bell B J, Bailey J, Stites E, Kuske J, Waisner B, Voytik-Harbin S L; Polymerization and matrix physical properties as important design considerations for soluble collagen formulations, *Biopolymers* (2010) 93(8):690-707, U.S. Patent Application Publication Number 20080268052, or U.S. Patent Application Publication Number 20120027732, each of which is incorporated herein by reference.

In various illustrative embodiments, the collagen for use in the methods and compositions described herein can be obtained from any suitable source of collagen known in the art. Exemplary collagen sources include submucosa tissues (U.S. Pat. Nos. 4,902,508, 5,281,422, and 5,275,826), pericardial tissue, urinary bladder submucosa tissue, stomach submucosa tissue, liver basement membrane tissue, placental tissue, ovarian tissue, animal tail tissue, skin tissue (e.g., Gallop, et al., Preparation and Properties of Soluble Collagens, *Meth. Enzymol.* 6: 635-641 (1963), incorporated herein by reference), and extracellular matrix tissues generally. In various embodiments, the type of collagen for use in the methods and compositions described herein can be any suitable type of collagen, including, but not limited to, Type I collagen, Type II collagen, Type III collagen, or Type IV collagen, or combinations thereof.

In one embodiment, a tissue enriched in collagen oligomers (e.g., pig skin tissue) can also be used to obtain the collagen for use in the methods and compositions described herein, or the collagen can be obtained from cells producing collagen oligomers (e.g., cells altered by recombinant techniques to express collagen oligomers), or by chemically crosslinking the collagen to obtain collagen oligomers (e.g., using a cross-linking agent known in the art). In various embodiments, the collagen for use in the methods and compositions described herein can comprise oligomers or can consist of oligomers. In another embodiment the collagen can comprise oligomers, and other forms of collagen such as monomers, telocollagen, and/or atelocollagen.

In another embodiment, the collagen can be soluble collagen or solubilized collagen. In the embodiments where the collagen is soluble collagen or solubilized collagen, the collagen is substantially free of insoluble collagen, but may contain some insoluble collagen. In another embodiment, the collagen consists of soluble collagen or solubilized collagen.

In various illustrative embodiments, the collagen, the collagen composition, the collagen matrix, the collagen solution, the lyophilized collagen, and/or the buffer solution can be sterilized using sterilization techniques known in the art, including but not limited to, propylene oxide or ethylene oxide treatment, gas plasma sterilization, gamma radiation (e.g., 1-4 mrads), ultraviolet radiation (e.g., UVC irradiation), electron beam, viral filtration, sterile filtration (e.g., with a 0.22 µm filter), chloroform exposure, and/or peracetic acid sterilization, and combinations thereof. In this embodiment, the sterilization procedure should not adversely affect the structure of collagen, the polymerization properties of the collagen, or the biological properties of the collagen that is sterilized. In various embodiments, the collagen can be sterilized before or after lyophilization (lyophilization procedures are described below).

In the ultraviolet radiation (e.g., UVC irradiation) embodiment, the collagen matrix that results from collagen polymerization can maintain a polymerization property relative to collagen that is not irradiated, a collagen composition this is not irradiated, a collagen matrix that is not irradiated, a collagen solution that is not irradiated, or lyophilized collagen that is not irradiated, respectively. In this embodiment, the polymerization property can be selected from shear storage modulus, elastic modulus (Young's modulus), tensile modulus, compressive modulus, fibril architecture, proteolytic degradation, cellular signaling, and combinations thereof. In various embodiments, the ultraviolet radiation dose (e.g., UVC irradiation) can range from about 5 mJ/cm$^2$ to about 800 mJ/cm$^2$, about 5 mJ/cm$^2$ to about 700 mJ/cm$^2$, about 5 mJ/cm$^2$ to about 600 mJ/cm$^2$, about 5 mJ/cm$^2$ to about 500 mJ/cm$^2$, about 5 mJ/cm$^2$ to about 400 mJ/cm$^2$, about 5 mJ/cm$^2$ to about 300 mJ/cm$^2$, 5 mJ/cm$^2$ to about 200 mJ/cm², 5 mJ/cm² to about 100 mJ/cm², 5 mJ/cm² to about 50 mJ/cm², about 30 mJ/cm² to about 800 mJ/cm², about 30 mJ/cm² to about 700 mJ/cm², about 30 mJ/cm² to about 600 mJ/cm², about 30 mJ/cm² to about 500 mJ/cm², about 30 mJ/cm² to about 400 mJ/cm², about 30 mJ/cm² to about 300 mJ/cm², about 30 mJ/cm² to about 200 mJ/cm², about 30 mJ/cm² to about 100 mJ/cm², about 30 mJ/cm² to about 50 mJ/cm², about 200 mJ/cm² to about 800 mJ/cm², about 300 mJ/cm² to about 800 mJ/cm², about 400 mJ/cm² to about 800 mJ/cm², about 500 mJ/cm² to about 800 mJ/cm², about 600 mJ/cm² to about 800 mJ/cm², about 50 mJ/cm² to about 300 mJ/cm², about 100 mJ/cm² to about 300 mJ/cm², or about 200 mJ/cm² to about 300 mJ/cm². In all of the ultraviolet radiation embodiments (e.g., UVC irradiation) described herein, the sterilization inactivates viruses. In this embodiment, "inactivates viruses" means inactivating all viruses, whether infectious or not, reducing the number of infectious viruses, or inhibiting the activity of viruses, whether infectious or not.

In one aspect, the collagen for use in the methods and compositions described herein can be purified by methods known in the art for purifying collagen. As used herein, "purified" means removing contaminants including, but not limited to, cellular contaminants, nucleotide contaminants, and endotoxins. In various embodiments, the collagen can be purified by removing contaminants so that it is at least about 90%, at least about 91%, at least about 92%, at least about 93%, at least about 94%, at least about 95%, at least about 96%, at least about 97%, at least about 98%, at least about 99%, or at least about 99.5% pure. In another embodiment the collagen can be isolated. As used herein "isolated" means substantially free of contaminants including, but not limited to, cellular contaminants, nucleotide contaminants, and endotoxins.

In one illustrative embodiment, the collagen for use in the methods and compositions described herein can be lyophilized and then reconstituted to form the collagen composition for mixing with the buffer solution as described herein. In this embodiment, the reconstitution of the lyophilized collagen is not a mixing step for polymerization of the collagen. As used herein, the term "lyophilized" means that water is removed from the protein, compound, or composition, by, for example, freeze-drying under a vacuum. Any lyophilization method known to the skilled artisan can be used. In one aspect, the collagen can be lyophilized in an acid, for example, acetic acid, hydrochloric acid, formic acid, lactic acid, citric acid, sulfuric acid, or phosphoric acid. In another embodiment, the collagen can be lyophilized in water. In other illustrative embodiments, cryoprotectants or lyoprotectants, or combinations thereof, can be used during the lyophilization.

In one illustrative aspect, the lyophilized collagen can be reconstituted to form the collagen composition described herein for mixing with the buffer solution to polymerize the collagen. In various illustrative embodiments, the collagen can be reconstituted in an acidic solution or in water. In various embodiments, the acidic solution can comprise acetic acid, hydrochloric acid, formic acid, lactic acid, citric acid, sulfuric acid, or phosphoric acid. In illustrative embodiments, the acidic solution for reconstitution can have a concentration of the acid of from about 0.005 N to about 0.1 N, from about 0.005 N to about 0.08 N, from about 0.005 N to about 0.06 N, from about 0.005 N to about 0.04 N, from about 0.005 N to about 0.02 N, from about 0.005 N to about 0.01 N, or about 0.01 N. In one embodiment, the acid can be hydrochloric acid and the hydrochloric acid can be about 0.005 N to about 0.1 N hydrochloric acid. In another embodiment, the acid can be hydrochloric acid and the hydrochloric acid can be about 0.01 N hydrochloric acid.

In one illustrative aspect, the collagen concentration in the collagen composition or in the collagen solution can be from about 0.1 mg/ml to about 40 mg/ml, from about 0.1 mg/ml to about 5 mg/ml, or from about 0.5 mg/ml to about 4 mg/ml. In other embodiments, the collagen concentration in the collagen composition or in the collagen solution can be from about 0.05 to about 5.0 mg/ml, about 1.0 mg/ml to about 3.0 mg/ml, about 0.05 mg/ml to about 10 mg/ml, about 0.05 to about 20 mg/ml, about 0.05 to about 30 mg/ml, about 0.05 to about 40 mg/ml, about 0.05 to about 50 mg/ml, about 0.05 to about 60 mg/ml, about 0.05 to about 80 mg/ml, about 5 mg/ml to 10 mg/ml, about 5 mg/ml to 20 mg/ml, about 5 mg/ml to about 40 mg/ml, about 5 mg/ml to 60 mg/ml, about 5 mg/ml to about 100 mg/ml, about 20 mg/ml to about 40 mg/ml, about 20 mg/ml to 60 mg/ml, or about 20 mg/ml to about 100 mg/ml.

In an illustrative embodiment, the collagen composition is mixed in a single step with the buffer solution to polymerize the collagen. In another embodiment, the collagen composition is mixed with the buffer solution in the absence of magnesium or manganese ions to polymerize the collagen. In one embodiment, the collagen composition is mixed with the buffer solution to form the collagen solution and the collagen solution is incubated at a temperature greater than about 25° C. to promote polymerization of the collagen in the collagen solution. In another embodiment, the collagen solution can be incubated at about 37° C. to promote polymerization of the collagen in the collagen solution. In various other embodiments, the collagen solution can be incubated at about 25° C., 26° C., 27° C., 28° C., 29° C., 30° C., 31° C., 32° C., 33° C., 34° C., 35° C., 36° C., 38° C., 39° C., or 40° C., to promote polymerization of the collagen in the collagen solution. In another embodiment, the collagen solution can be incubated at from about 25° C. to about 40° C. to promote polymerization of the collagen in the collagen solution. In other embodiments, the polymerization can be conducted at temperatures above 20° C., or at a temperature selected from the range of about 20° C. to about 40° C. In these embodiments, the collagen can be polymerized to form fibrils similar to those found in the body.

In one embodiment, the buffer solution to be mixed with the collagen composition to form the collagen solution can comprise about 0.03 mM to about 0.2 mM $MgCl_2$, about 0.002 mM to about 0.02 mM $MgCl_2$, less than about 0.02 mM $MgCl_2$, or no $MgCl_2$. In other embodiments, the buffer solution to be mixed with the collagen composition to form the collagen solution can comprise about 0.3 mM to about 3 mM $KH_2PO_4$, about 1 mM to about 10 M $Na_2HPO_4$, about 0.1 mM to about 4 mM KCl, about 0.02 M to about 0.3 M NaCl, and about 0.002 N to about 0.02 N NaOH. In another embodiment, the buffer solution to be mixed with the collagen composition to form the collagen solution can comprise about 0.5 weight percent to about 5 weight percent of glucose, about 0.5 weight percent glucose or less, or no glucose.

In one aspect, the buffer solution can be diluted from a 10×, 5×, 2×, or any suitable starting concentration, to make a 1× buffer solution having any of the component concentrations in the preceding paragraph. In one aspect, the kit described herein can contain a buffer solution with a concentration of 10×, 5×, or 2×, or any suitable starting concentration, for dilution to make a 1× buffer solution. In accordance with one embodiment, the 10× buffer solution can comprise the following ingredients at the following concentrations:

1.37 M NaCl
0.027 M KCl
0.081 M Na$_2$HPO$_4$
0.015 M KH$_2$PO$_4$
0.1 N NaOH
and, optionally, 55.5 mM glucose In another embodiment, a 1× buffer solution can comprise the following ingredients at the following concentrations:
0.137 M NaCl
0.0027 M KCl
0.0081 M Na$_2$HPO$_4$
0.0015 M KH$_2$PO$_4$
0.01 N NaOH
and, optionally, 5.55 mM glucose In these embodiments, NaOH is present in the buffer solution. In conventional previously known methods for polymerizing collagen, the NaOH was added separately as an additional mixing step in the methods for polymerization of collagen. In another illustrative embodiment, calcium chloride can be present in the buffer solution at a concentration of about 0.4 mM to about 2.0 mM.

In various embodiments, the buffer in the buffer solution may be selected from the group consisting of phosphate buffer saline (PBS), Tris (hydroxymethyl) aminomethane Hydrochloride (Tris-HCl), 3-(N-Morpholino) Propanesulfonic Acid (MOPS), piperazine-n,n'-bis (2-ethanesulfonic acid) (PIPES), [n-(2-Acetamido)]-2-Aminoethanesulfonic Acid (ACES), N-[2-hydroxyethyl]piperazine-N'-[2-ethanesulfonic acid] (HEPES), and 1,3-bis [tris(Hydroxymethyl)methylamino]propane (Bis Tris Propane). In one embodiment the buffer is PBS.

In various illustrative embodiments, the pH of the collagen solution for the polymerization of collagen is selected from the range of about 5.0 to about 11, about 6.0 to about 9.0, about 6.5 to about 8.5, and in another embodiment the pH is about 7.3 to about 7.4.

In various embodiments, nutrients, including minerals, amino acids, sugars, peptides, proteins, vitamins, or glycoproteins that facilitate cellular proliferation, such as laminin and fibronectin, hyaluronic acid, or growth factors such as epidermal growth factor, platelet-derived growth factor, transforming growth factor beta, or fibroblast growth factor, and glucocorticoids such as dexamethasone, can be added to the collagen solution before or after collagen polymerization is complete or during collagen polymerization. In accordance with another embodiment, cells can be added to the collagen solution before or after collagen polymerization is complete or during collagen polymerization. In various embodiments, the cells can be selected from the group consisting of epithelial cells, endothelial cells, mesodermally-derived cells, mesothelial cells, synoviocytes, neural cells, glial cells, osteoblasts, fibroblasts, chondrocytes, tenocytes, smooth muscle cells, skeletal muscle cells, cardiac muscle cells, multi-potential progenitor cells (e.g., stem cells, including bone marrow progenitor cells), adipocytes, and osteogenic cells.

In one embodiment, a collagen matrix prepared according to the any of the methods described herein is provided. In one aspect, the collagen matrix can be a medical graft. In one embodiment, the medical graft has a use selected from the group consisting of a tissue graft material, an injectable graft material, a wound dressing, a hemostatic dressing, a delivery vehicle for therapeutic cells, and a delivery vehicle for a therapeutic agent. In another embodiment, the methods described herein may be used to make a bioink formulation for printing tissues or organs. In another embodiment, the collagen matrix is used for research purposes, such as drug toxicity testing or drug development. In one embodiment, the matrices prepared by the methods described herein can serve as substrates for the regrowth of endogenous tissues at the implantation site (e.g., remodeling) and the matrices can have the characteristics of the damaged or diseased tissues that they replace at the site of implantation or injection.

In one illustrative embodiment, the matrices described herein can contain fibrils with a fibril area fraction (defined as the percent area of the total area occupied by fibrils in a cross-sectional surface of the matrix) or a fibril volume fraction (the percent area of the total area occupied by fibrils in 3 dimensions) of about 0.1% to about 100%, about 0.5% to about 100%, about 0.5% to about 26%, about 1% to about 100%, about 1% to about 26%, about 1% to about 7%, about 1% to about 15%, of about 7% to about 26%, about 20% to about 30%, about 20% to about 50%, about 20% to about 70%, about 20% to about 100%, about 30% to about 50%, about 30% to about 70%, or about 30% to about 100%, and/or a modulus (e.g., an elastic or linear modulus (defined by the slope of the linear region of the stress-strain curve obtained using conventional mechanical testing protocols; i.e., stiffness), a compressive modulus, or a shear storage modulus) of about 0.5 kPa to about 40 kPa, about 30 kPa to 100 kPa, about 30 kPa to about 1000 kPa, about 30 kPa to about 10000 kPa, about 30 kPa to about 70000 kPa, about 100 kPa to 1000 kPa, about 100 kPa to about 10000 kPa, or about 100 kPa to about 70000 kPa.

In another embodiment, a kit comprising lyophilized collagen, a hydrochloric acid solution, and a buffer solution is described. In yet another embodiment, a kit comprising a collagen composition and a buffer solution is provided. In these kit embodiments, the buffer solution can comprise about 0.03 mM to about 0.2 mM MgCl$_2$, about 0.002 mM to about 0.02 mM MgCl$_2$, less than about 0.02 mM MgCl$_2$, or the buffer solution does not comprise MgCl$_2$. In various embodiments, the buffer solution further comprises about 0.003 M to about 0.03 M KH$_2$PO$_4$, about 0.01 M to about 00.1 M Na$_2$HPO$_4$, about 0.001 M to about 0.04 M KCl, about 0.2 M to about 3.0 M NaCl, and about 0.02 N to about 0.2 N NaOH. In another aspect, the buffer solution can comprise about 0.2 weight percent to about 5 weight percent of glucose, about 0.5 weight percent glucose or less, or no glucose.

In one aspect, in the kit embodiment having a hydrochloric acid solution, the hydrochloric acid solution can comprise about 0.005 N hydrochloric acid to about 0.1 N hydrochloric acid. In one aspect, in the kit embodiment having lyophilized collagen, a hydrochloric acid solution, and a buffer solution the lyophilized collagen, the hydrochloric acid solution, and the buffer solution are in separate containers. In one aspect of the embodiment having the collagen composition and the buffer solution, the collagen in the collagen composition can be at a concentration of about 0.1 mg/ml to about 40 mg/ml or about 0.1 mg/ml to about 5 mg/ml. In this embodiment, the collagen composition and the buffer solution can be in separate containers, such as sterilized vials or separate compartments of a dual syringe comprising a mixing element. In any of the kit embodiments described herein, the kit can comprise instructions for use of components of the kit. In any of the kit embodiments described herein, the buffer solution is capable of polymerizing collagen using a single mixing step comprising mixing the buffer solution with the lyophilized collagen reconstituted in the hydrochloric acid solution or with the collagen composition.

In another embodiment, a kit is provided with collagen in a lyophilized form and the kit further comprises a buffer solution as described herein and a solution of an acid, such as acetic acid, or another dilute acid including for example, hydrochloric acid, formic acid, lactic acid, citric acid, sulfuric acid, or phosphoric acid for reconstituting the lyophilized collagen.

The following examples illustrate specific embodiments in further detail. These examples are provided for illustrative purposes only and should not be construed as limiting the invention in any way.

Example 1

Preparation of Collagen Composition

Type I collagen oligomers were derived from the dermis of closed herd pigs and prepared as described previously (Bailey J L, Critser P J, Whittington C, Kuske J L, Yoder M C, Voytik-Harbin S L; Collagen oligomers modulate physical and biological properties of three-dimensional self-assembled matrices, *Biopolymers* (2011) 95(2):77-93 and Kreger S T, Bell B J, Bailey J, Stites E, Kuske J, Waisner B, Voytik-Harbin S L; Polymerization and matrix physical properties as important design considerations for soluble collagen formulations, *Biopolymers* (2010) 93(8):690-707, both incorporated herein by reference). Prior to use, lyophilized collagen oligomers were dissolved in 0.01 N hydrochloric acid. Research-grade oligomer was rendered aseptic by chloroform exposure at 4° C. Medical-grade oligomer was sterile filtered using a 0.22 gm Millex-GP PES Express syringe filter (Millipore, SLGPO33RS). A Sirius Red (Direct Red 80) assay was used to determine collagen concentration. Oligomer formulations were standardized based upon purity as well as polymerization capacity according to the ASTM international consensus standard F3089-14 (ASTM Standard F3089, 2014, "Standard Guide for Characterization and Standardization of Polymerizable Collagen-Based Products and Associated Collagen-Cell Interactions", ASTM International, West Conshohocken, PA, F3089-14). Polymerization capacity is defined by matrix shear storage modulus (G') as a function of collagen concentration of the polymerization reaction. Multi-step self-assembly was performed and involved 3 reagents-10× Polymerization Buffer PLUS, 0.1N NaOH, and Polymerization Supplement. Single-step self-assembly was performed with 10× self-assembly reagents (diluted 1:10) prepared according to the following recipe in the absence of $MgCl_2$:

2 g $KH_2PO_4$ (FW 136.09)
11.5 g $Na_2HPO_4$ (FW 141.96)
2 g KCl (FW 74.55)
10 g glucose
80 g NaCl (FW 58.44)
20 ml 5N NaOH All reagents were added to Milli-Q filtered water to achieve a finalized volume of 1 liter and sterile filtered (0.22 μm). Integra Flowable was obtained from Integra Life Sciences (Plainsboro, NJ) and handled according to manufacturer's instructions.

Example 2

Viscoelastic Properties Testing

Viscoelastic properties of self-assembled collagen matrices were determined using oscillatory shear mode on an AR2000 rheometer (TA Instruments, New Castle, DE) as previously described (Kreger et al., 2010). Samples were polymerized on the rheometer stage for 30 min followed by a shear-strain sweep from 0.1% to 4% strain at 1 Hz. The shear storage modulus (G') at 1% strain was used as a measure of matrix stiffness.

Example 3

Cell Culture and Preparation of Three-Dimensional Collagen-Fibril Tissue Constructs Low-passage human adipose-derived stem cells (hASC) were obtained from Zen-Bio (Research Triangle Park, NC) and cultured in growth medium consisting of Dulbecco's Modified Eagle Medium (DMEM; Life Technologies, Carlsbad, CA), 10% fetal bovine serum (FBS), 100 U/mL penicillin, and 100 U/mL streptomyosin (Invitrogen, Grand Island, NY). The hASC were grown and maintained in a humidified environment of 5% carbon dioxide in air at 37° C. Cells were kept below 80% confluence and used in experiments at passage 6 to 9.

Cell-encapsulated collagen-fibril tissue constructs were prepared by suspending hASC (300,000 cells/ml) in neutralized oligomer (200 Pa) solutions. Neutralization was achieved using multi-step or single-step procedures and reagents. Tissue constructs were fixed in 3% paraformaldehyde after 3 days of culture and stained with phalloidin for visualization of the actin cytoskeleton. For 3D qualitative analysis, tissue constructs were imaged using an Olympus FluoView FV-1000 confocal system adapted to an inverted microscope (IX81, Olympus Corporation, Tokyo, Japan).

Example 4

Mouse Subcutaneous Injection

C57BL/6 mice (n=5) obtained from Harlan Laboratories (Indianapolis, Indiana) were initially anesthetized in a 1 L induction chamber and then maintained unconscious with a coaxial nose cone non-rebreathing system that administered 1-3% isoflurane in 1.5 L/min medical grade air. Sterile eye lubricant was applied and animals were positioned on an adjustable heated stage set to 44° C. to maintain internal body temperature near 37° C. Heart rate, respiration rate, and body temperature were monitored every 15 minutes with stage electrodes and a rectal probe, respectively. Hair on the dorsal side was removed with clippers and depilatory cream (Nair, Church & Dwight Co., Inc. Ewing, NJ). Experimental groups included 1) research-grade oligomer (500 Pa), 2) medical-grade oligomer (500 Pa), 3) Integra Flowable, 4) phosphate buffered saline (PBS), or 5) no treatment control. Oligomer, Integra Flowable, and PBS formulations were injected (200 μl) subcutaneously on both sides of the back, parallel to the sagittal plane. Oligomer and PBS formulations were administered using 27 G, Y2 inch needles, while Integra Flowable required 18 G, ½ inch needles because of material consistency and clogging of smaller needle sizes. After four weeks, animals were euthanized and implant sites harvested along with generous margins of surrounding host tissue. All specimens were fixed in formalin, paraffin-embedded, thin-sectioned, and stained with hematoxylin and eosin (H&E) and Masson's trichrome.

Example 5

Development and Validation of Single-Step Self-Assembly Procedure and Reagent

Figure 2:
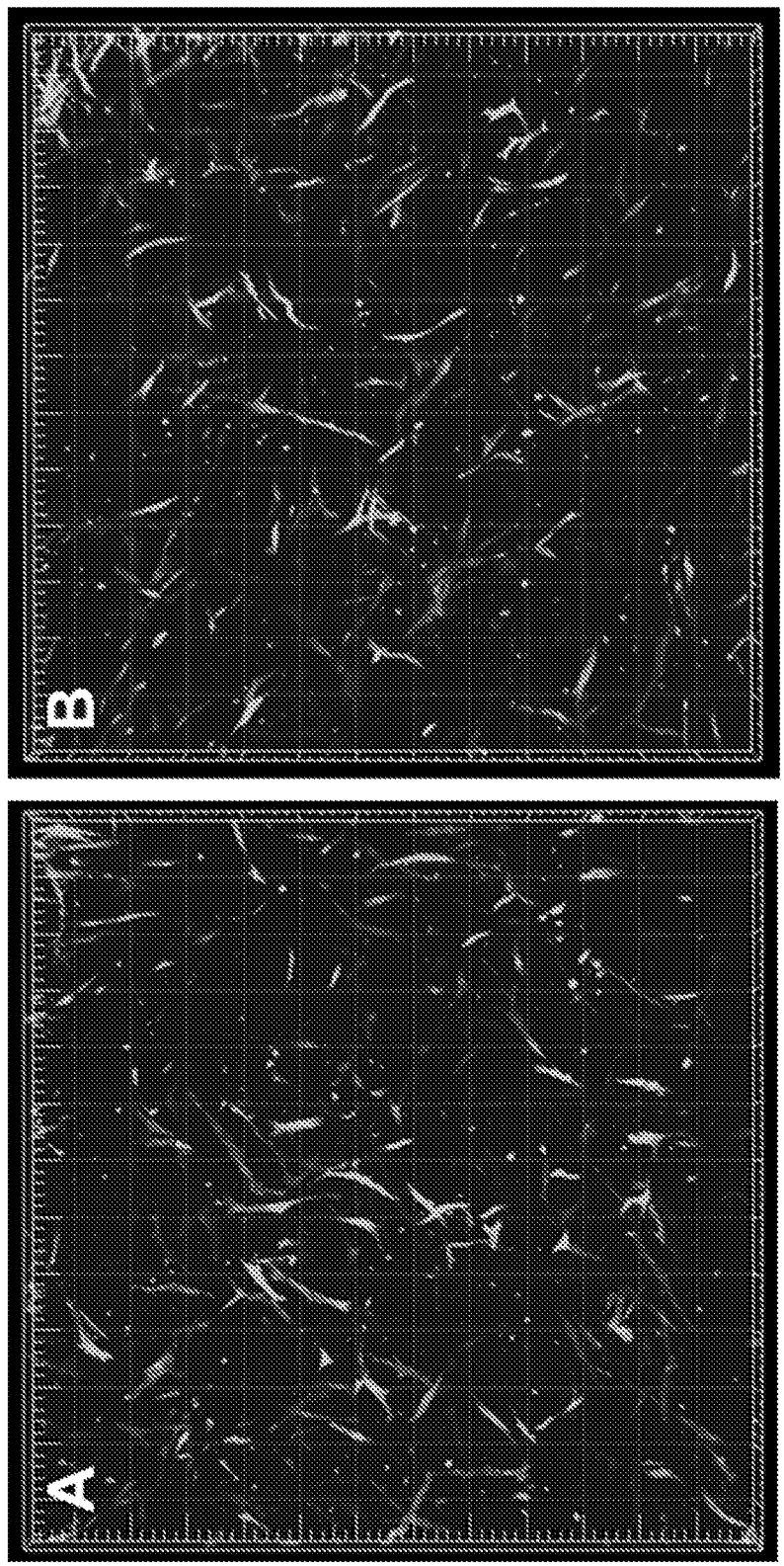
FIG. 2 shows that self-assembled matrices prepared with a multi-step and single-step procedures show similar biocompatibility and cellular response. Human adipose-derived stem cells were used to create three-dimensional collagen-fibril tissue constructs using a multi-step (FIG. 2a) or single-step (FIG. 2b) procedures. After 4 days, constructs were fixed, stained with phalloidin, and visualized using confocal microscopy.
Figure 3:
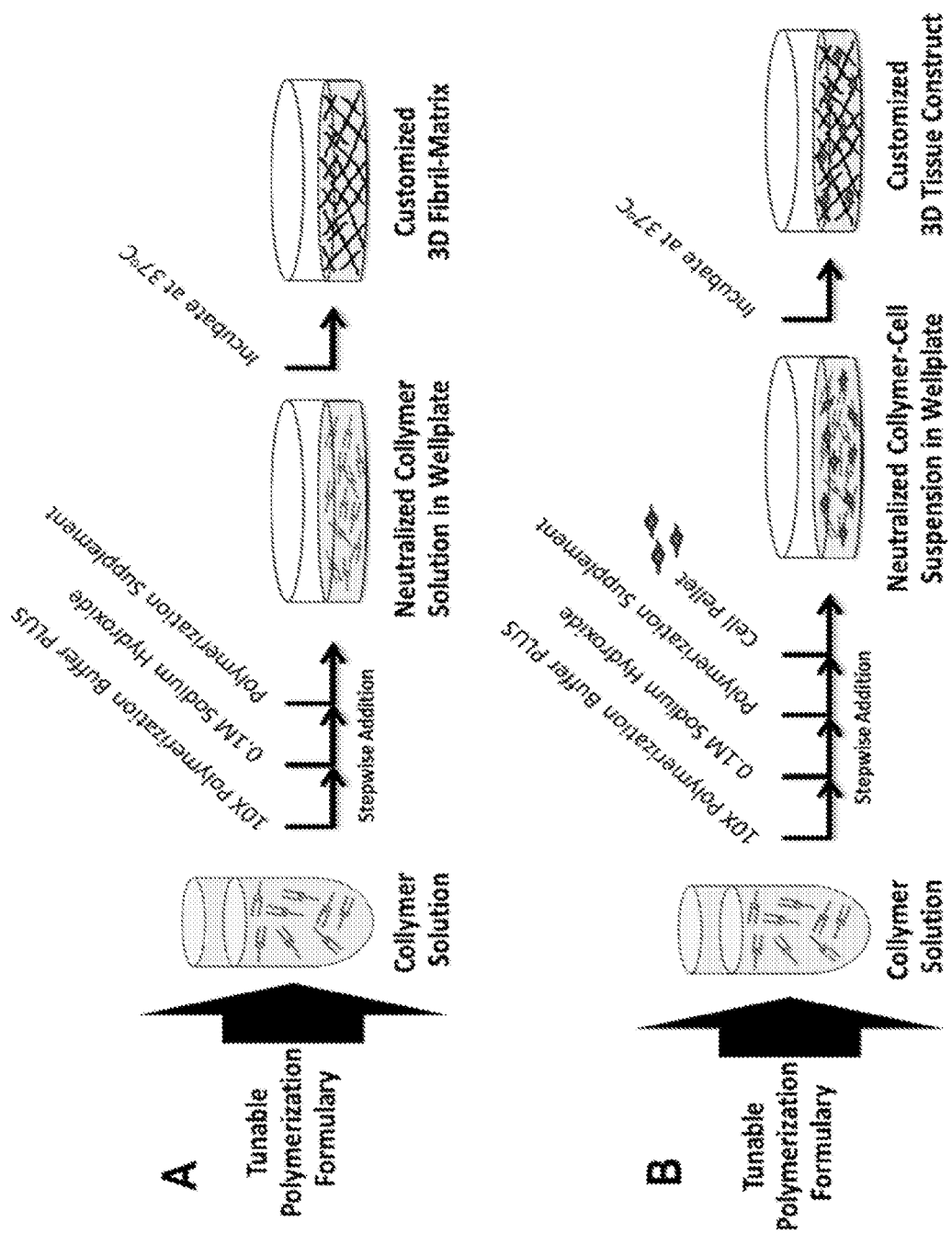
FIG. 3 shows a multi-step procedure.
Figure 4:
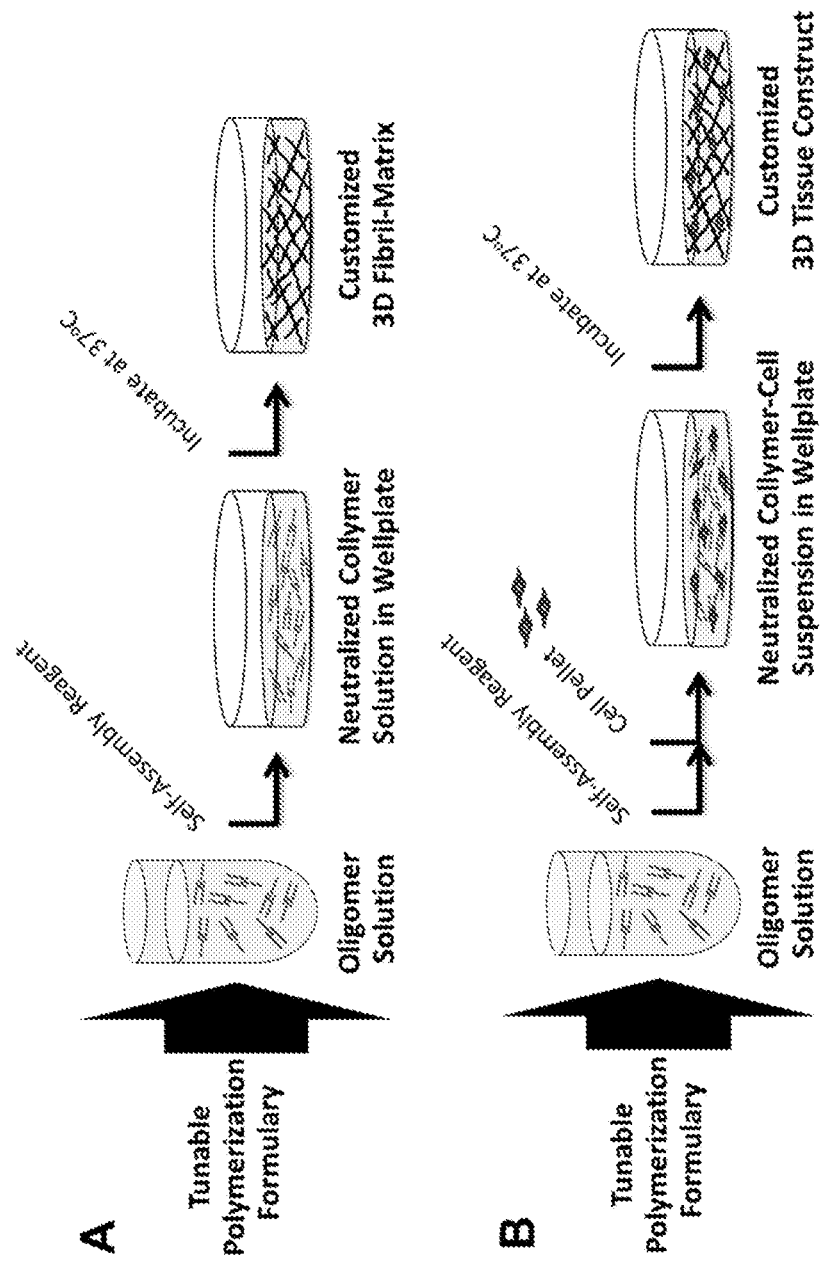
FIG. 4 shows a single-step procedure.

The single-step self-assembly procedure and reagent included maintenance of i) physiologically relevant conditions and reagents and ii) polymerization capacity as observed with an established multi-step procedure. Initial attempts to combine all reagents used in a multi-step procedure, including 10× Polymerization Buffer PLUS, Polymerization Supplement, and NaOH, resulted in an unstable solution that formed a flocculent precipitate. However, when $MgCl_2$ was removed, no precipitation was noted, even when stored at 4° C. for extended periods of time. Based upon these results, follow-up studies were performed to evaluate the polymerization capacity and in vitro cell response. When compared to multi-step procedures, the single-step procedure yielded similar polymerization capacity curves and similar in-vitro cell behavior and morphology as shown in FIGS. 1 and 2, respectively. Preliminary studies have also been conducted to show utility of single-step self-assembly for three-dimensional bioprinting applications. More specifically, Oligomer, 10× Self-Assembly Reagent, and a diluent have been employed to print tissue constructs containing continuous gradients in collagen-fibril density using a custom-designed single nozzle bioprinting device. The new single-step collagen self-assembly procedure and associated formulary are shown in FIGS. 3 and 4, respectively.

Example 6

Development and Validation of Collagen Polymer Sterilization

Figure 5:
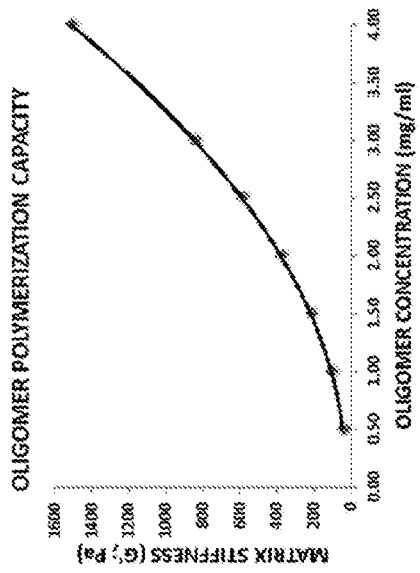
FIG. 5 shows the formulary supporting user customization of self-assembled collagen matrices using a single-step procedure based on starting collagen oligomer concentration.
Figure 6:
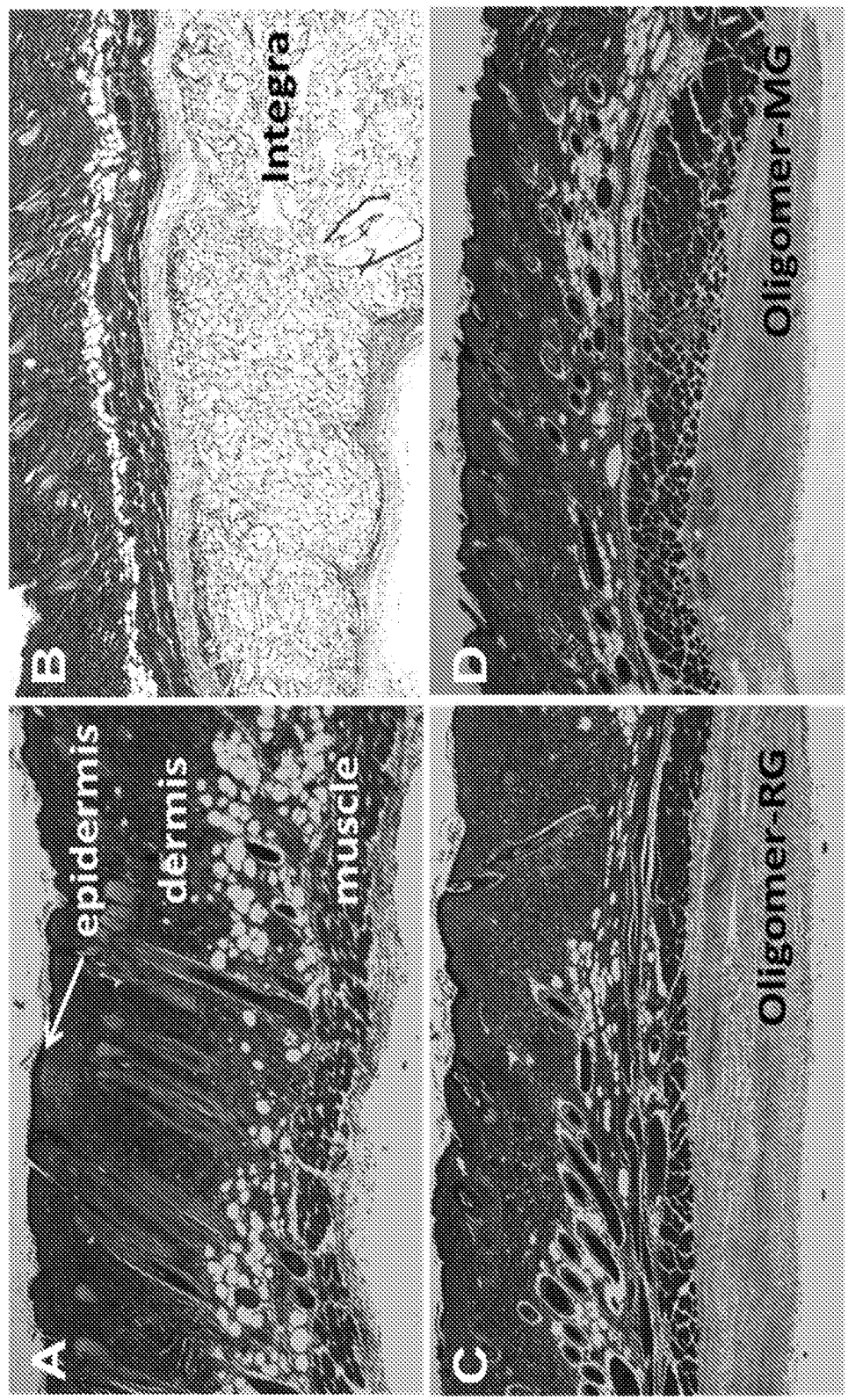
FIG. 6 shows that research-grade and medical-grade formulations of oligomer show similar non-inflammatory tissue regeneration responses following subcutaneous injection in mice. Research-grade oligomer, medical-grade oligomer, and Integra Flowable were subcutaneously injected (200 ul) in mice. After 4 weeks, implant sites were harvested, fixed, and prepared for histopathological analysis. Images show cross-sections of untreated skin (control; A), Integra Flowable (B), research-grade oligomer (C), and medical-grade oligomer (D).

Additional studies were performed to evaluate sterilization methods that would support scale-up manufacturing and regulatory approval of medical-grade oligomer products. Sterile filtration was employed using a conventional 0.22 μm syringe-based filter device. Because oligomer represents a soluble molecular solution, it is amenable to sterile filtration. Oligomer formulation (500 Pa) showed statistically similar (p>0.05) polymerization kinetics and capacity before (458±55 Pa) and after (434±49) sterile filtration. Additional studies confirmed that similar in vivo tissue responses were obtained with research-grade and medical-grade oligomer formulations. Furthermore, the in-vivo tissue response obtained using single-step polymerization of research-grade oligomer was consistent with those obtained using multi-step polymerization procedures (see FIG. 5).

Example 7

Figure 7:
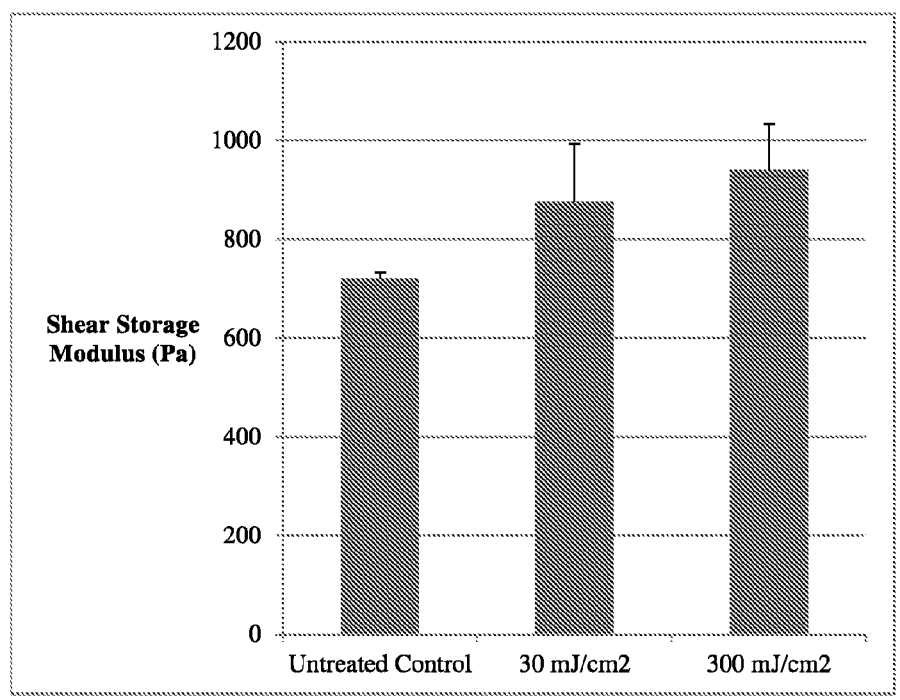
FIG. 7 shows the shear storage modulus of collagen matrices polymerized from collagen treated with UVC irradiation at doses of 0 (untreated control), 30 mJ/cm² (1 minute of irradiation), and 300 mJ/cm² (10 minutes of irradiation).

Effects of Ultraviolet Irradiation of Collagen on the Properties of the Collagen Matrix Monochromatic ultraviolet radiation at 254 nm (UVC) was produced by a flat-plate collimated beam system, employing a low-pressure Hg lamp source. Thin layers (1 mm) of collagen solution were placed in petri dishes and treated with UVC doses of 0 (untreated control), 30 mJ/cm$^2$ (1 minute of irradiation) and 300 mJ/cm$^2$ (10 minutes of irradiation). The polymerization capacity and associated viscoelastic properties of the treated samples were measured as described in Example 2 and compared to untreated controls. Shear storage modulus measurements were statistically similar for oligomer solutions exposed to 0, 30, and 300 mJ/cm$^2$ doses of UVC irradiation (FIG. 7).

What is claimed is:

1. A method for preparing a matrix, said method comprising polymerizing oligomeric collagen, using a single mixing step for the polymerization, said method comprising mixing an oligomeric collagen composition with a buffer solution to form a collagen solution wherein the buffer solution comprises a base and less than 00.2 mM $MgCl_2$, wherein the buffer and the base are in the same composition when mixed with the oligomeric collagen composition for polymerization of the oligomeric collagen, and wherein the polymerization of the oligomeric collagen in the collagen solution results in formation of the matrix.

2. The method of claim 1 wherein the oligomeric collagen composition, the collagen solution, or the matrix is sterilized by a method selected from the group consisting of exposure to chloroform, viral filtration, sterile filtration, ultraviolet radiation, gamma irradiation, E-beam, and combinations thereof.

3. The method of claim 1 wherein the buffer solution does not comprise $MgCl_2$.

4. A method for preparing a collagen matrix, said method comprising polymerizing oligomeric collagen using a single mixing step, wherein said mixing step consists of mixing a solution comprising soluble oligomeric collagen with a buffer solution to form a mixed collagen solution, wherein said buffer solution comprises less than 0.02 mM $MgCl_2$, 0.003 M to 0.03 M $KH_2PO_4$, 0.1 M to 0.1 M $Na_2HPO_4$, 0.001 M to 0.04 M KCl, 0.2 M to 3.0 M NaCl, and 0.02 N to 0.2 N NaOH, and wherein said mixing step induces the polymerization of the soluble oligomeric collagen in the mixed collagen solution resulting in the formation of the collagen matrix.

5. The method of claim 4 wherein the solution comprising soluble oligomeric collagen, the mixed collagen solution, or the collagen matrix is sterilized by a method selected from the group consisting of exposure to chloroform, viral filtration, sterile filtration, ultraviolet radiation, gamma irradiation, E-beam, and combinations thereof.

6. The method of claim 2 wherein the oligomeric collagen composition, the collagen solution, and/or the matrix is sterilized using ultraviolet radiation.

7. The method of claim 6 wherein the matrix that results from collagen polymerization maintains a polymerization property relative to a matrix formed from a collagen composition this is not irradiated, a matrix formed from a collagen solution that is not irradiated, or a matrix that is not irradiated.

8. The method of claim 7 wherein the polymerization property is selected from shear storage modulus and an in vivo tissue response.

9. The method of claim 6 wherein the radiation dose ranges from about 30 mJ/cm$^2$ to about 300 mJ/cm$^2$.

10. The method of claim 6 wherein the sterilization inactivates viruses.

11. The method of claim 5 wherein the solution comprising soluble oligomeric collagen, the mixed collagen solution, and/or the collagen matrix is sterilized using ultraviolet radiation.

12. The method of claim 11 wherein the collagen matrix that results from collagen polymerization maintains a polymerization property relative to a collagen matrix that results from a solution comprising soluble oligomeric collagen that is not irradiated, a collagen matrix that results from a mixed collagen solution that is not irradiated, or a collagen matrix that is not irradiated.

13. The method of claim 12 wherein the polymerization property is selected from shear storage modulus and an in vivo tissue response.

14. The method of claim 11 wherein the radiation dose ranges from about 30 mJ/cm$^2$ to about 300 mJ/cm$^2$.

15. The method of claim 11 wherein the sterilization inactivates viruses.

16. The method of claim 1 wherein the base is NaOH.

17. The method of claim 16 wherein the buffer solution comprises about 0.02 N to about 0.2 N NaOH.

18. The method of claim 1 wherein the collagen solution maintains polymerization capacity relative to oligomeric collagen polymerized using a multi-step procedure.

19. The method of claim 4 wherein the solution comprising soluble oligomeric collagen maintains polymerization capacity relative to oligomeric collagen polymerized using a multi-step procedure.

* * * * *